United States Patent [19]

McVicker

[11] 4,302,400
[45] Nov. 24, 1981

[54] HETERONUCLEAR NOBLE METAL CLUSTER CATALYSTS

[75] Inventor: Gary B. McVicker, Westfield, N.J.

[73] Assignee: Exxon Research & Engineering Co., Florham Park, N.J.

[21] Appl. No.: 147,064

[22] Filed: May 5, 1980

Related U.S. Application Data

[62] Division of Ser. No. 101,423, Dec. 10, 1979, which is a division of Ser. No. 924,161, Jul. 13, 1978, Pat. No. 4,217,249.

[51] Int. Cl.$^3$ ............................................. C07F 15/00
[52] U.S. Cl. .......................... 260/429 R; 252/466 PT
[58] Field of Search ..................................... 260/429 R

[56] References Cited

U.S. PATENT DOCUMENTS

| | | | |
|---|---|---|---|
| 3,954,821 | 5/1976 | Herskovitz et al. | 260/429 R |
| 3,989,799 | 11/1976 | Brown | 260/429 R X |
| 4,048,093 | 9/1977 | Knifton | 260/429 R X |
| 4,115,433 | 9/1978 | Cosby et al. | 260/429 R X |
| 4,180,517 | 12/1979 | Vidal et al. | 260/429 R |
| 4,199,520 | 4/1980 | Cosby et al. | 260/429 R |
| 4,201,728 | 5/1980 | Hughes | 260/429 R |
| 4,217,249 | 8/1980 | McVicker | 252/466 PT |

Primary Examiner—Helen M. S. Sneed
Attorney, Agent, or Firm—Edward M. Corcoran

[57] ABSTRACT

New heteronuclear noble metal cluster complexes have been discovered and synthesized for the first time. These complexes are (pyridine)$_2$ Pt[Ir$_6$(CO)$_{15}$], (pyridine)$_2$-Pt[Ir$_2$(CO)$_7$], (pyridine)$_3$ Pt[Ru$_3$(CO)$_{12}$], ((C$_6$H$_5$)$_3$P)$_2$-Pt[Ir(CO)$_3$P(C$_6$H$_5$)$_3$]$_2$, ((C$_6$H$_5$)$_3$P)$_2$Rh(CO)[Ir(CO)$_4$], and (pyridine)$_2$ Pt[Rh(CO)$_2$(P(C$_6$H$_5$)$_3$)$_2$]$_2$.

These new heteronuclear noble metal cluster complexes are useful as supported mixed noble metal catalyst precursors. These new cluster complexes, of known stoichiometry, are deposited on anhydrous refractory inorganic oxide or carbon supports and then reduced resulting in the formation of a supported heteronuclear noble metal catalyst having the same metals stoichiometry as the starting cluster complexes. In this way, precise control can be exercised over the ratio and distribution of multiple metal components in a mixed noble metal catalyst. The usage of preformed heteronuclear noble metal cluster complexes as supported mixed metal catalyst precursors maximizes surface alloy formation and also yields unique mixed-metal cluster structures on the support surface.

2 Claims, 14 Drawing Figures

PROPOSED STRUCTURE FOR
((C$_6$H$_5$)$_3$P)$_2$ Rh(CO)[Ir(CO)$_4$]

PROPOSED STRUCTURE FOR (PYRIDINE)$_2$ Pt [Ir$_6$(CO)$_{15}$]

PROPOSED STRUCTURE FOR (PYRIDINE)$_2$ Pt [Ir$_2$(CO)$_7$]

PROPOSED STRUCTURE FOR ((C$_6$H$_5$)$_3$P)$_2$ Pt [Ir(CO)$_3$ P(C$_6$H$_5$)$_3$]$_2$

PROPOSED STRUCTURE FOR (PYRIDINE)$_3$ Pt [Ru$_3$(CO)$_{12}$]

PROPOSED STRUCTURE FOR ((C$_6$H$_5$)$_3$P)$_2$ Rh(CO)[Ir(CO)$_4$]

COMPARISON OF 0.4% Ir/0.067% Pt/0.47% Cl/Al$_2$O$_3$ CATALYSTS

COMPARISON OF 0.4% Ir/0.067% Pt/0.47% Cl/Al$_2$O$_3$ CATALYSTS

COMPARISON OF 0.4% Ir/0.067% Pt/$Al_2O_3$ CATALYSTS

NAPHTHA REFORMING OVER 0.4% Ir/0.067% Pt/0.7% $Cl/Al_2O_3$ CATALYSTS

HETERONUCLEAR NOBLE METAL CLUSTER CATALYSTS

This is a division, of application Ser. No. 101,423, filed Dec. 10, 1979, which is a Rule 60 Division of Ser. No. 924,161, filed July 13, 1978.

New heteronuclear noble metal cluster complexes have been discovered and synthesized for the first time. These complexes are:

(pyridine)$_2$Pt[Ir$_6$(CO)$_{15}$],
(pyridine)$_2$Pt[Ir$_2$(CO)$_7$],
(pyridine)$_3$Pt[Ru$_3$(CO)$_{12}$],
((C$_6$H$_5$)$_3$P)$_2$Pt[Ir(CO)$_3$P(C$_6$H$_5$)$_3$]$_2$,
((C$_6$H$_5$)$_3$P)$_2$Rh(CO)[Ir(CO)$_4$],
(pyridine)$_2$Pt[Rh(CO)$_2$(P(C$_6$H$_5$)$_3$)$_2$]$_2$ These new heteronuclear noble metal cluster complexes are useful as supported heteronuclear noble metal catalyst precursors. These new cluster complexes of known stoichiometry, are deposited from nonaqueous solutions onto anhydrous refractory inorganic oxide support materials (ceramics, powders, beads, extrudates, etc.) or carbon and then reduced, resulting in the formation of a supported heteronuclear noble metal catalyst having the same metals stoichiometry as the starting cluster complexes. In this way precise control can be exercised over the ratio, distribution, and dispersion of multiple metal components in a mixed noble metal catalyst. The usage of preformed heteronuclear noble metal cluster complexes as supported catalyst precursors maximizes surface alloy formation and also yields unique mixed metal cluster structures on the support surface.

Supported heteronuclear noble metal cluster complex catalysts prepared from the recited heteronuclear noble metal cluster complexes exhibit greater activity and lower coking rates for catalytic hydrocarbon conversion reactions than conventionally prepared supported mixed noble metal catalysts of the same nominal metals concentration.

These supported heteronuclear noble metal cluster catalysts utilize as supports materials selected from the group consisting of anhydrous refractory inorganic oxides and carbon, preferably the refractory inorganic oxides (in powder or extrudate form), more preferably Al$_2$O$_3$, SiO$_2$, SiO$_2$-Al$_2$O$_3$, the Group IVB, Group VB, Group VIB, manganese, magnesium, calcium, barium and strontium oxides, most preferably, alumina.

The supported heteronuclear noble metal cluster complex catalysts prepared from the corresponding supported carbonyl complexes have metal loadings within the range of 0.001 to 5.0 wt. % platinum (or rhodium) the other metal components being present at a wt. % in conformity with the stoichiometry of the heteronuclear noble metal cluster complexes.

Expressed in other terms, the total heterometal loading is within the range of 0.002 to 35 wt. % based on total catalyst weight, the amount of each metal present being determined by the stoichiometry of the heteronuclear noble metal complex precursor. Preferably, the total heterometal loading is in the range of 0.002 to 10 wt. % based on total catalyst weight.

The catalyst may also contain, when desirable, a halogen, preferably fluorine and/or chlorine. The amount of halogen present, is within the range of 0.001 to 3.0 wt. % based on total catalyst composition, preferably 0.1 to 2.5 wt. %, most preferably 0.5 to 2.0 wt. %. The halogen can be added to the catalyst after deposition of the cluster complex precursor or can be added to the support prior to deposition of the catalyst precursor, i.e. the heteronuclear noble metal cluster complexes. Preferably, the halogen is chlorine.

The use of transition metal carbonyl complexes for the preparation of supported metal catalyst is a new area of research of particular inerest to catalytic chemists. Monomeric metal carbonyl complexes such as Ni(CO)$_4$ have been used to prepare supported catalysts, e.g. Ni/Al$_2$O$_3$ catalysts (see Parkyns, N. D., "Proceedings 3rd International Congress on Catalysis", (W. H. M. Sachtler, G. C. A. Schuit & P. Zweitering, Eds.) p. 194, North-Holland, Amsterdam, 1965). The use of metal cluster complexes (defined here as complexes containing more than one transition metal of a single type) as supported catalyst precursors has, however, only recently been suggested (see Anderson, J. R. and Mainwaring, D. E., J. Catalysis, 35, 162 (1974), Anderson, J. R., Elmes, P. S., Howe, R. F. and Mainwaring, D. E., J. Catalysis, 50, 508 (1977) and Ichikawa, M., J. Chem. Soc. Chem. Comm., 11 (1976). The utilization of heteronuclear cluster complexes (defined here as complexes containing at least two different transition metals) as precursors for the generation of supported heterometallic catalysts has likewise received very little attention. Furthermore, heterometallic cluster complexes in which the heterometal atoms are noble metals (as opposed to First Period Group VIII metals) have not heretofore been employed as supported catalyst precursors.

The instant invention relates to a new and improved preparation of supported heterometal noble metal catalysts containing at least two different noble metals selected from the group Ru, Rh, Ir and Pt via the usage of novel, especially formulated heterometal noble metal cluster complexes. The heterometal noble metal cluster catalysts derived by the deposition, and subsequent reduction of preformed heterometal noble metal cluster complexes have been found to be exceptionally active and selective hydrocarbon conversion catalysts.

Conventional heterometallic noble metal catalysts are prepared by the impregnation of a suitable support with an aqueous solution containing the appropriate metal salts followed by drying and reduction. The multiple salt impregnation step can be either sequential or simultaneous. In such preparations the clustering of metal atoms to form heteronuclear clusters on the support surface is not well-defined. In conventional aqueous impregnations of supports, pH changes often occur within the salt solution. Such pH changes can lead to metal aggregation processes which in turn yield poorly dispersed supported metal phases (e.g. Ru/Al$_2$O$_3$ and Pt/SiO$_2$-Al$_2$O$_3$) in the finished catalyst. The formation of supported heteronuclear clusters also requires that the different metal salts are absorbed onto the support surface at equivalent rates. This situation is known not to generally occur (see Harriott, P., J. Catalysis, 14, 43 (1969)). In general then, the chemistry leading to complete and uniform clustering (alloying) of heterometal atoms on support surfaces is not well understood and/or readily controlled.

In concert with the proper choice of support, the use of heteronuclear cluster complexes as heterogeneous catalyst precursors offers numerous advantages. These include: (1) the preparation of supported catalysts exhibiting well-dispersed and uniform heterometal cluster phases, (2) the supported heterometal clusters may retain the unique geometries of the starting heteronuclear cluster complexes, (3) extremely efficient clustering of the heterometals on the support surface is likely since the precursor complexes are held together by strong heterometal metal-metal bonds, and (4) the surface heterometal stoichiometry can be systematically varied by employing precursor cluster complexes of different known compositions, stoichiometries and structures.

The number of heteronuclear noble metal cluster complexes commercially available or reported in the literature is extremely limited. The instant specification discloses new noble metal cluster complexes which have been discovered. The ultimate use of such heteronuclear noble metal cluster complexes is for the preparation of novel supported heteronuclear noble metal cluster catalysts which find utility in a wide variety of hydrocarbon conversion reactions. The novel heteronuclear noble metal cluster complexes disclosed in the instant application were in general prepared by metathetical exchange reactions.

Figure 1:
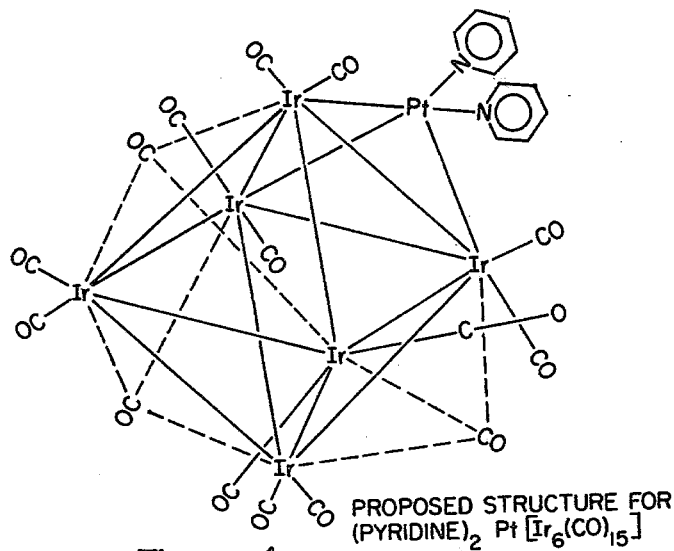
FIGS. 1 through 5 inclusive are schematic representations of proposed molecular structures of supported heteronuclear noble metal cluster catalysts of this invention.

A. Preparation of Heteronuclear Noble Metal Cluster Complexes

Air sensitive reactions and catalyst preparations using air sensitive materials were carried out in a "dry box" employing a purified nitrogen atmosphere. Solvents used in heteronuclear noble metal complex and supported heteronuclear noble metal cluster catalyst preparations were dried and degassed by standard techniques.

(1) pyridine)$_2$Pt[Ir$_6$(CO)$_{15}$]

This new composition was prepared by the metathetical reaction between Na[Ir$_6$(CO)$_{15}$] (see L. Malatesta, G. Caglio and M. Angoletta, *Chem. Comm.*, 532 (1970)) and cis-(pyridine)$_2$PtCl$_2$ (see G. B. Kauffman, *Inorg. Syn.*, 7, 251 (1963)) in THF solution. The complex is a dark red solid and is readily soluble in moderately polar organic solvents such as THF or methylene chloride. The complex is rapidly decomposed in air but is stable indefinitely under nitrogen. A pure product was obtained (75% yield) by recrystallizing the crude material from a 50/50 mixture of THF/n-pentane. The complex was found to contain (%): C, 17.3; H, 1.37; N, 1.45; Pt, 10.1; Ir, 60.1; O, 13.3; Cl, 0.02; calculated %: C, 15.6; H, 0.52; N, 1.45; Pt, 10.1; Ir, 59.9; O, 12.5; Cl, nil. The infrared bands in the carbonyl region for the (pyridine)$_2$Pt[Ir$_6$(CO)$_{15}$](hereafter identified as PtIr$_6$) complex in the solid state and in solution in THF are listed in Table I. These spectra are characterized by a pair of strong bands near 2010 and 1975 cm$^{-1}$. These bands are readily assigned to terminal carbonyl stretching frequencies. Weak to medium intensity bands in the 1780-1730 cm$^{-1}$ region are assigned to bridging carbonyl groups. The infrared spectra of the Ir$_6$(CO)$_{15}$⊖ dianion (Na or NH$_4$ salt) in THF solution are characterized by a strong terminal carbonyl band near 1970 cm$^{-1}$ and bridging carbonyl modes near 1780 and 1730 cm$^{-1}$. Upon interaction of the Ir$_6$(CO)$_{15}$⊖ dianion with (pyridine)$_2$Pt(++), the terminal bands of the Ir$_6$(CO)$_{15}$⊖ dianion are shifted by about 40 cm$^{-1}$ to higher wave numbers. Such a frequency shift is consistent with a transfer of electron density from the Ir$_6$(CO)$_{15}$⊖ dianion onto the Pt(++) center. This electronic rearrangement implies the formation of a covalent bond (bonds) between the Pt atom and the Ir$_6$(CO)$_{15}$ cluster. The carbonyl band positions of the bridging carbonyl groups are not appreciably changed by this interaction. A reasonable structure for the PtIr$_6$ cluster complex is presented in FIG. I where only the metal atoms are shown for simplicity. In the proposed structure the Pt atom is assumed to be bonded to a face on the octahedral Ir$_6$(CO)$_{15}$ cluster. The coordination about the Pt atom is completed by two pyridine molecules. The local symmetry of the Pt atom is probably close to square planar. Within the Ir$_6$(CO)$_{15}$ cluster each Ir atom is assumed to possess two terminal carbonyl groups. The remaining three carbonyl groups must then occupy bridging positions on alternating faces of the Ir$_6$ octahedron.

The proposed structure of the PtIr$_6$ cluster complex, however, does not in any way restrict the well-defined stoichiometric relationship between the Pt and Ir atoms in the discrete molecule and is presented merely by way of explanation.

(2) (pyridine)$_2$Pt(Ir$_2$(CO)$_7$)

This novel cluster complex was prepared for the first time by the metathetical reaction between Na(Ir(CO)$_4$) and trans-(pyridine)$_2$PtCl$_2$ (see G. B. Kauffman, *Inorg. Syn.* 7, 251 (1963)) in the THF solution. The Na[Ir(CO)$_4$] intermediate was prepared by the sodium amalgam reduction of either (Ir(CO)$_3$Cl)$_x$ or Ir$_4$(CO)$_{12}$ in THF solution under 70-75 psig of carbon monoxide. The Pt-Ir complex is a red-brown solid and is readily soluble in moderately polar organic solvents such as THF or methylene chloride. The complex is extremely air sensitive, but can be stored under nitrogen. A pure product was obtained (86% yield) by recrystallizing the crude material from a 50/50 mixture of THF/n-pentane. The complex was found to contain (%): Pt, 19.6; Ir, 42.5; calculated (%): Pt, 20.8; Ir, 41.0.

The unique (pyridine)$_2$Pt[Ir$_2$(CO)$_7$] complex (hereafter identified as PtIr$_2$) was prepared by the metathetical reaction between trans-(py)$_2$PtCl$_2$ and Na[Ir(CO)$_4$] in THF solution. The product from this reaction was expected to be trans(pyridine)$_2$Pt[Ir(CO)$_4$]$_2$ (see equation 1). An analogous trans(pyridine)$_2$Pt[Co(CO)$_4$]$_2$ complex, prepared according to equation 1 except that

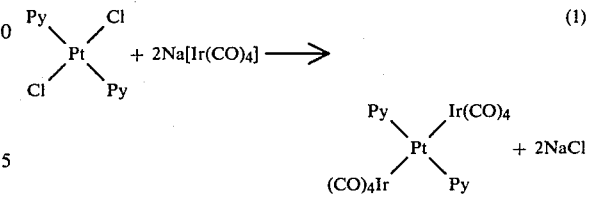

(1)

Py = pyridine
Na[Co(CO)$_4$] was used in place of Na[Ir(CO)$_4$], exhibits carbonyl bands at 2025s, 1975s and 1900 sh cm$^{-1}$ (see R. G. Pearson and J. Dehand, *J. Organometallic Chem.*, 16 485 (1969)). A structurally similar Ir complex would be expected to display carbonyl bands in the same region. The PtIr$_2$ complex was found, however, to display four carbonyl bands in the terminal region (2040-1900 cm$^{-1}$) in the solid state and in solution in THF. In addition to the strong terminal carbonyl bands a strong bridging carbonyl band near 1730 cm$^{-1}$ was present in the solid and solution spectra of the PtIr$_2$ complex. A triangular (diphos)Pt[Co$_2$(CO)$_7$] has been prepared by the reaction of (diphos)PtCl$_2$ (chloride ions cis) with Na[Co(CO)$_4$] in THF solution (equation 2). The (diphos)PtCo$_2$ cluster complex exhibits carbonyl bands (KBr pellet) at

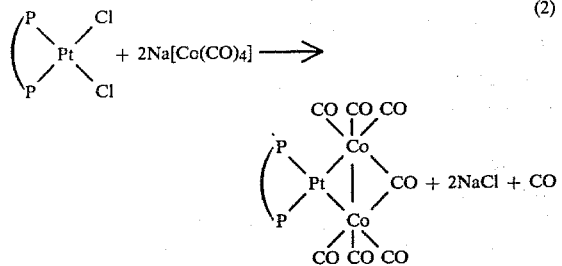

(2)

Figure 2:
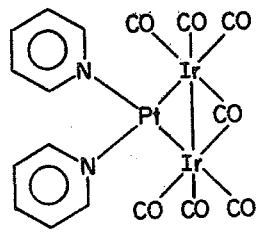

$\overgroup{P\ P}$=bis(diphenylphospheno)ethane=diphos 2049s, 2010s, 1952 vs, 1970sh and 1729s cm$^{-1}$. The 1729 cm$^{-1}$ band has been assigned to the bridging carbony group. (See J. Dehand and J. F. Nennig, *Inorg. Nucl. Chem. Letters*, 10, 875 (1974). The infrared spectrum of solid PtIr$_2$ is very similar to that displayed by the (diphos)Pt-Co$_2$ complex. This suggests that the PtIr$_2$ complex adopts an analogous structure (FIG. 2). To obtain this structure, it must be assumed that an initially formed trans-(pyridine)$_2$Pt[Ir(CO)$_4$]$_2$ complex (intermediate) undergoes a trans to cis isomerization. Accompanying the isomerization is the expulsion of one mole of carbon monoxide and the formation of an Ir-Ir bond. The formation of an Ir-Ir bond is suggested to preserve the 18 electron rule for the Ir atoms. The terminal carbonyl bands exhibited by PtIr$_2$ are centered about 90 cm$^{-1}$ to higher energy than the Ir(CO)$_4$$^\ominus$ anion. This shift to higher energy suggests that the electron density on the Ir atoms in the PtIr$_2$ complex is lower than in the Ir(CO)$_4$$^\ominus$ anion. The distribution of electronic charge indicated by the infrared implies the formation of a covalent interaction between the two Ir atoms and the Pt atom. The geometry about the Pt atom is probably close to square-planar with the two pyridine molecules and the two Ir atoms occupying mutually cis positions. Each Ir atom is assumed to be six-coordinate with approximate octahedral symmetry.

3 (Ch$_6$H$_5$)$_3$P)$_2$Pt[Ir(CO)$_3$P(C$_6$H$_5$)$_3$]$_2$

This new composition was prepared by the exchange reaction between trans-((C$_6$H$_5$)$_3$P)$_2$PtCl$_2$ and Na[Ir(CO)$_3$P(C$_6$H$_5$)$_3$] in THF solution. The Na[Ir(CO)$_3$P(C$_6$H$_5$)$_3$] intermediate was prepared by the reduction of a THF solution of ((C$_6$H$_5$)$_3$P)$_2$Ir(CO)Cl with sodium amalgam under 70 psig carbon monoxide at 140° F. for 24 hours (see J. P. Collman, F. D. Vastine and W. R. Roper, *J. Amer. Chem. Soc.*, 90, 2282 (1968). The Pt-Ir complex is a yellow-orange solid and is readily soluble in common organic solvents. The complex is moderately stable in air. A pure product was obtained (69% yield) by recrystallizing the crude material from benzene. The complex was found to contain (%): Pt, 10.8; Ir, 21.4; Cl, nil; calculated (%): Pt, 10.9; Ir, 21.4; Cl, nil. The complex is essentially monomeric in benzene solution (M.W. found: 1640; M.W. calculated: 1790).

Figure 3:
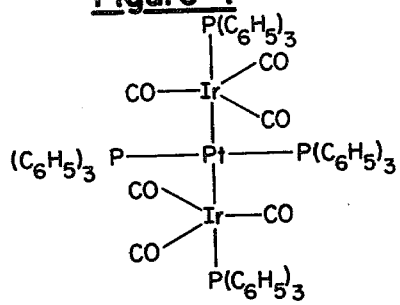

The ((C$_6$H$_5$)$_3$P)$_2$Pt[Ir(CO)$_3$P(C$_6$H$_5$)$_3$]$_2$ complex (hereafter identified as L$_2$PtIr$_2$) was found to exhibit in the solid state and in THF solution five to six terminal carbonyl bands in the 2080-1900 cm$^{-1}$ region. The band maxima is centered near 1960 cm$^{-1}$. This maxima is located 90-100 cm$^{-1}$ to higher energy than the major band displayed by the [Ir(CO)$_3$P(C$_6$H$_5$)$_3$]$^\ominus$ anion in THF solution. The higher energy bands exhibited by L$_2$PtIr$_2$, in contrast to the anion, suggests the presence of relatively covalent Pt-Ir bonds. The proposed covalent Pt-Ir interaction is supported by the fact that a covalent Hg[Ir(CO)$_3$P(C$_6$H$_5$)$_3$]$_2$ complex exhibits high energy carbonyl bands at 1945 and 1985 cm$^{-1}$. The formation of covalent Pt-Ir bonds is further suggested by the complexity of the carbonyl bands displayed by L$_2$PtIr$_2$. If local C$_{3v}$ symmetry rules were obeyed by the Ir(CO)$_3$P(C$_6$H$_5$)$_3$ moiety, only two infrared active carbonyl bands would be allowed. The presence of additional bands is assumed to result from vibrational coupling between two trans Ir(CO)$_3$P(C$_6$H$_5$)$_3$ groups through the Pt atom. The two weak bands in the 1800-1750 cm$^{-1}$ region most likely arise from a small Ir$_2$Pt$_2$(P(C$_6$H$_5$)$_3$)$_4$(CO)$_6$ impurity. A proposed structure for the L$_2$PtIr$_2$ complex is shown in FIG. 3.

The three carbonyl groups and phosphine ligand bonded to each Ir atom are omitted for simplicity. The symmetry about the Pt atom is probably close to square planar. Each Ir atom is assumed to be five coordinate with the phosphine and Pt atom occupying apices. Three equivalent carbonyl groups are assumed to complete the trigonal plane. The inability of L$_2$PtIr$_2$ to form a closed PtIr$_2$ cluster as observed for (pyridine)$_2$Pt[Ir$_2$(CO)$_7$] is likely the result of steric interference. The bulky phosphine must force the [Ir(CO)$_3$P(C$_6$H$_5$)$_3$] moieties to occupy transpositions about the Pt atom. Such a geometry would not allow a close approach of the Ir atoms which would facilitate the formation of a closed PtIr$_2$ system containing an Ir-Ir bond.

4 (Pyridine)$_3$Pt[Ru$_3$(CO)$_{12}$]

This new complex was prepared by the metathetical reaction between cis-(pyridine)$_2$PtCl$_2$ and Na$_2$[Ru$_3$(CO)$_{12}$] in THF solution in the presence of excess pyridine. The Na$_2$[Ru$_3$(CO)$_{12}$] intermediate was prepared for the first time by the sodium amalgam reduction of Ru$_3$(CO)$_{12}$ under 70 psig carbon monoxide. The red-brown Pt-Ru complex is moderately stable in air, as no decomposition was noted upon standing in air for several hours. The complex is readily soluble in THF, but exhibits limited solubility in nonpolar solvents such as benzene. A pure product was obtained by recrystallizing the crude material from a 20/80 mixture of THF/n-pentane. The Pt-Ru complex was found to contain (%): C, 29.3; H, 1.94; N, 4.00; O, 19.4; Pt, 17.7; Ru, 27.6; calculated (%): C, 30.3; H, 1.41; N, 3.92; O, 17.9; Pt, 18.2; Ru, 28.3.

The Ru$_3$(CO)$_{12}$$^\ominus$ dianion intermediate (Na salt) exhibits five carbonyl bands in the 2030-1890 cm$^{-1}$ region. The major terminal carbonyl band is centered near 1950 cm$^{-1}$. A weak to medium band at 1649 cm$^{-1}$ is due to a small unknown impurity. The Ru$_3$(CO)$_{12}$$^\ominus$ dianion is a new species and is probably generated by the reduction of a single Ru-Ru bond in the starting Ru$_3$(CO)$_{12}$ complex. Complete reduction of the Ru$_3$(CO)$_{12}$ cluster would have been expected to yield Na$_2$Ru(CO)$_4$ (carbonyl band near 1800 cm$^{-1}$ expected). The effect of localized charge is demonstrated by the isoelectronic series Fe(CO)$_4$$^\ominus$ (1788), Co(CO)$_4$$^\ominus$ (1883), and Ni(CO)$_4$(2057) where the carbonyl stretching frequency (cm$^{-1}$) increases with decreasing charge on the metal center. The major band exhibited by the Ru$_3$(CO)$_{12}$$^\ominus$ dianion is intermediate in energy between those shown by Co(CO)$_4$$^\ominus$ and Ni(CO)$_4$.

Figure 4:
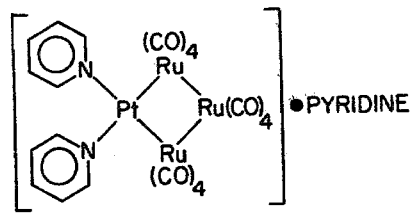

This suggests that the two negative charges are delocalized over the three Ru atom framework. The effective charge is then probably close to two thirds of an electron per Ru atom. Upon complexation of the $Ru_3(CO)_{12}{\ominus}$ dianion with a Pt $\oplus\oplus$ center, the infrared band contour remains nearly the same but the band maxima is shifted about 50 cm$^{-1}$ to higher energy (1950→2000 cm$^{-1}$ shift). This frequency shift suggests the formation of covalent Pt-Ru bonds. Weak bands at 1804 and 1763 cm$^{-1}$ in the spectrum of (pyridine)$_3$Pt-(Ru$_3$(CO)$_{12}$) (hereafter identified as PtRu$_3$) suggests the presence of a small amount of unknown impurity. Based upon elemental analyses, infrared spectroscopy and the well known tendency for Pt $\oplus\oplus$ complexes to adopt a square planar configuration, a reasonable structure for the PtRu$_3$ complex is presented in FIG. 4. The four terminal carbonyl groups bonded to each Ru atom have been omitted for simplicity. The Pt atom is assumed to be square planar with two pyridine molecules and the two end Ru atoms of the Ru$_3$(CO)$_{12}$ moiety occupying mutually cis-positions. Such a structure is rationalized by assuming displacement of chloride ions from cis-(pyridine)$_2$PtCl$_2$ by the Ru$_3$(CO)$_{12}{\ominus}$ dianion. The third mole of pyridine is assumed to be present as a molecule of crystallization to preserve a square planar Pt atom. Each Ru atom is assumed to possess four terminal carbonyl groups. Relatively intense bands in the 1800-1700 cm$^{-1}$ region would be expected if the PtRu$_3$ complex contained a significant number of bridging carbonyl groups. The proposed bonding scheme represents the first example of a closed PtRu$_3$ ring system.

5. $((C_6H_5)_3P)_2Rh(CO)[Ir(CO)_4]$

This novel heteronuclear noble metal cluster complex was prepared by the metathetical reaction between $((C_6H_5)_3P)_2Rh(CO)Cl$ and $NaIr(CO)_4$. The solid heteronuclear Rh-Ir complex is dark red and is readily soluble in moderately polar organic solvents such as THF, benzene or methylene chloride. The complex is rapidly decomposed in air but is stable indefinitely under nitrogen. A pure product (90% yield) was obtained by recrystallizing the crude material from a 50/50 mixture of THF/n-pentane. The complex was found to contain (%): Rh, 10.5; Ir, 19.8; Cl, 0.01; calculated (%): Rh, 10.7; Ir 20.0; Cl, nil.

Figure 5:
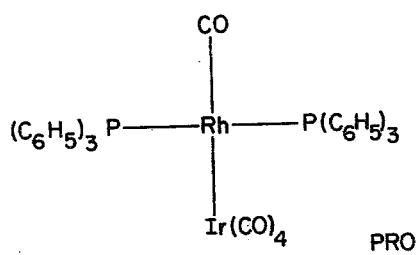

The starting $((C_6H_5)_3P)_2Rh(CO)Cl$ and $Na[Ir(CO)_4]$ complexes exhibit carbonyl stretching frequencies at 1965 s and 1896 vs and 1863 sh cm$^{-1}$, respectively, in THF solutions. The new $((C_6H_5)_3P\ Rh(CO)[Ir(CO)_4]$ (hereafter identified as RhIr) complex exhibits carbonyl bands at 2042 w, 1995 sh, 1987 vs, 1962 sh and 1932 m cm$^{-1}$ in THF solution. The shift in carbonyl band positions to higher wave numbers upon complexing the Ir(CO)$_4{\ominus}$ anion to a Rh$\oplus$ center as well as the complexity of the spectrum, suggests the formation of a covalent Rh-Ir bond. The absence of carbonyl bands below 1900 cm$^{-1}$ further suggests the presence of terminal carbonyl groups only. A reasonable structure for the Rh-Ir complex is shown in FIG. 5. The bonding about the Rh atom is likely to be either square planar or slightly distorted toward tetrahedral symmetry while the local symmetry about the Ir atom is most probably $C_{3v}$.

6. (pyridine)$_2$Pt[Rh(CO)$_2$(P(C$_6$H$_5$)$_3$)$_2$]$_2$

This new cluster complex can be readily prepared by allowing trans-(pyridine)$_2$PtCl$_2$ to react with Na[Rh(CO)$_2$(P(C$_6$H$_5$)$_3$)$_2$] in THF solution. The Na[Rh(CO)$_2$(P(C$_6$H$_5$)$_3$)$_2$] salt is easily obtained by reducing $((C_6H_5)_3P)_2Rh(CO)Cl$ with a 1% Na amalgam in the presence of 40-60 psig carbon monoxide in THF solution (see page 10, lines 20-21). The cluster complex can be purified by recrystallizing the crude product from a 20/80 mixture of THF/n-pentane.

The novel heteronuclear noble metal cluster complexes disclosed herein were found to exhibit physical and chemical properties typical of covalent metal complexes. The cluster complexes are maintained in discrete molecular geometries by covalent metal-metal bonds. The heteronuclear metal-metal bonds remain intact in solution in nonpolar solvents. By varying metal stoichiometry, heteronuclear cluster complexes of different molecular structures were prepared.

These new heteronuclear noble metal cluster complexes will be used as precursors for the preparation of supported heteronuclear cluster catalysts which in turn find utility as active and selective hydrocarbon conversion catalysts.

B. Preparation of Supported Catalysts

Base case or standard catalysts were prepared by the aqueous impregnation of $\eta$-Al$_2$O$_3$ powders or $\gamma$-Al$_2$O$_3$ extrudates with the appropriate standardized transition metal salt solutions. Heteronuclear noble metal catalysts were prepared by co-impregnation with standardized aqueous salt solutions. Both incipient wetness (I.W.) and adsorption (ADS) impregnations were carried out. $\eta$-Al$_2$O$_3$ powders (BET surface areas 170-220 m$^2$/gm) were prepared by calcining beta aluminum tri-hydrate at 1100° F. under air for five hours. The $\gamma$-Al$_2$O$_3$ extrudates (BET surface areas 180-200 m$^2$/gm) were commercially available samples. The freshly impregnated catalysts were routinely dried overnight at 250°-280° F. and then reduced under 20% H$_2$/He (500-1200 cc/min) for several hours at an elevated temperature (790°-930° F.).

Supported heteronuclear noble metal cluster catalysts, defined as catalysts prepared by the deposition of preformed heteronuclear noble metal cluster complexes onto ceramic supports, were prepared under an inert atmosphere (N$_2$) since the precursor complexes were in many cases sensitive to air and moisture. The ceramic supports were dried at elevated temperatures 660°-1020° F. and outgassed prior to use to minimize hydrolysis of the starting complexes. Carefully dried organic solvents (THF or methanol), containing known amounts of the appropriate heteronuclear noble metal cluster complex, were employed as impregnation media. Both incipient wetness and adsorption impregnations were employed. Since the precursor complexes were chlorine free, the ceramic supports were in some cases prechlorided (aqueous HCl). Alternately, acidity was built into the supported cluster catalysts by treating reduced cluster catalysts with aqueous HCl. Freshly impregnated cluster catalysts were vacuum dried (10$^{-4}$ mm) at room temperature. The dry catalysts were then reduced with 20% H$_2$/He (500-1200 cc/min), with careful exclusion of air, for several hours at an elevated temperature (790°-930° F.). These reduction conditions were found to be sufficient to completely decompose the precursor heteronuclear noble metal cluster complexes on the support surface.

Analyses of selected Al$_2$O$_3$ supported standard and heteronuclear noble metal cluster catalysts are given in Table II. Analyses were performed on reduced and thus stabilized catalyst samples.

Characterization of Heteronuclear Noble Metal Cluster Complexes Supported on Alumina Infrared Spectroscopic Studies The preparation of supported heterometallic cluster complexes was outlined above. Prior to reduction, vacuum dried supported heteronuclear noble metal cluster catalysts were subjected to infrared measurements. Spectra in the carbonyl region were recorded on Nujol mull samples sandwiched between KBr salt plates. Infrared samples were prepared in the strict absence of oxygen and moisture.

A (pyridine)$_2$Pt[Ir$_6$(CO)$_{15}$] cluster complex on Al$_2$O$_3$ catalyst (nominally 0.4% Ir/0.067% Pt) was found to exhibit five terminal carbonyl bands in the 2070–1970 cm$^{-1}$ region (see Table III). The major band is centered near 2020 cm$^{-1}$. A weak to medium band near 1800 cm$^{-1}$ is assigned to the vibration of bridging carbonyl groups. The similarity in carbonyl band shapes and band positions between the supported PtIr$_6$ cluster and a mull spectrum of the solid PtIr$_6$ complex (Table I) suggests that the complex remains intact on the Al$_2$O$_3$ surface. The retention of bridging carbonyl bands further suggests the surface stability of Ir clusters. The supported PtIr$_6$ cluster is readily oxidized and undergoes rapid loss of carbonyl band intensity upon exposure to air. During the initial stages of oxidation new carbonyl surface species are produced. These species exhibit carbonyl band maxima near 2040 and 1630 cm$^{-1}$. The high wavenumber band suggests the presence of partially oxidized iridium carbonyl complexes. The low wavenumber band is assigned to an iridium carbonate surface species. Carbonate formation is presumably via oxidation of complexed carbon monoxide. A [(C$_2$H$_5$)$_4$N]$_2$[Ir$_6$(CO)$_{15}$] monometallic cluster on Al$_2$O$_3$ catalyst (nominally 0.4% Ir) was found to display four or five bands in the terminal carbonyl region (2015–1925 cm$^{-1}$). Bridging carbonyl bands in the 1800–1700 cm$^{-1}$ region were also present in the spectrum. The similarity in carbonyl band positions between the supported Ir$_6$ anion and the anion in THF solution suggests that the Ir$_6$ cluster is stable on the Al$_2$O$_3$ surface. The supported Ir$_6$ cluster is extremely air sensitive and rapidly loses carbonyl band intensity upon exposure to air. The intermediate oxidation products display carbonyl and carbonate bands at the same wavenumber positions as the supported PtIr$_6$ cluster complex. This result suggests that the sub-carbonyl species formed during oxidation of the suggested PtIr$_6$ cluster complex are associated with the iridium component.

The infrared spectrum of a (pyridine)$_2$Pt[Ir$_2$(CO)$_7$] cluster complex on Al$_2$O$_3$ catalyst (nominally 0.32% Ir/0.16% Pt) displays four or five terminal carbonyl bands in the 2070–1970 cm$^{-1}$ region. The major terminal carbonyl band is situated near 2010 cm$^{-1}$. Several weak to medium bands in the bridging carbonyl region (1800–1750 cm$^{-1}$) are also clearly present in the spectrum of the supported PtIr$_2$ complex. The general shape of the infrared carbonyl bands of the supported PtIr$_2$ cluster complex was found to be very similar to those exhibited by the solid PtIr$_2$ complex. The major carbonyl band of the PtIr$_2$ cluster complex is, however, shifted about 30 cm$^{-1}$ to higher energy upon deposition on the Al$_2$O$_3$ surface. This shift suggests that the PtIr$_2$ complex is interacting with the Al$_2$O$_3$ support surface. The energy shift is consistent with the transfer of electron density from the PtIr$_2$ cluster to the support (the electron transfer may be to a Lewis acid center on the Al$_2$O$_3$ surface). The bridging carbonyl band positions are also shifted to higher energy upon deposition of the PtIr$_2$ complex onto Al$_2$O$_3$. In contrast to the PtIr$_2$ complex, the PtIr$_6$ complex did not exhibit a pronounced shift in its infrared upon deposition onto Al$_2$O$_3$. These results may reflect the larger size of the PtIr$_6$ cluster within which a partially positive charge (generated by interaction with the Al$_2$O$_3$ support) could be more readily distributed. As was found for the supported PtIr$_6$ cluster, the supported PtIr$_2$ cluster was rapidly oxidized in air.

An ionic K[Ir(CO)$_4$] complex on Al$_2$O$_3$ catalyst (nominally 2% Ir) was found to display a rich infrared spectrum in the carbonyl region. The strong bands at 1892 and 1868 cm$^{-1}$ indicates the presence of ionic Ir(CO)$_4^\ominus$ surface species. Additional strong bands near 1995 and 1925 cm$^{-1}$ suggest the existence of partially oxidized iridium carbonyl complexes. The absence of bridging carbonyl bands suggests that clusters of iridium atoms are not present on the Al$_2$O$_3$ surface. Upon exposure to air the carbonyl bands due to the Ir(CO)$_4^\ominus$ anion and the partially oxidized iridium carbonyl surface species are rapidly reduced in intensity. The oxidation process is accompanied by growth of carbonyl bands near 2040 and 1635 cm$^{-1}$. The 2040 cm$^{-1}$ band, as discussed before, is most likely due to an oxidized iridium carbonyl surface species. The low energy band is reasonably assigned to an iridium carbonate surface complex.

A (pyridine)$_3$Pt[Ru$_3$(CO)$_{12}$] cluster on Al$_2$O$_3$ catalyst (nominally 0.33% Ru/0.22% Pt) was found to exhibit a mull spectrum very similar in detail to that displayed by the solid PtRu$_3$ complex. This result suggests that the PtRu$_3$ complex is not degraded on the Al$_2$O$_3$ surface. The intermediate Ru$_3$(CO)$_{12}^\ominus$ dianion on Al$_2$O$_3$ (nominally 2% Ru) was also found to be reasonably stable. In the case of the supported dianion (K salt) the major terminal carbonyl band near 2000 cm$^{-1}$ is about 50 cm$^{-1}$ to higher energy than the corresponding band of the dianion in THF solution. This suggests that the Ru$_3$(CO)$_{12}^\ominus$ dianion is partially oxidized by the underlying Al$_2$O$_3$ support. The fact that the PtRu$_3$ complex is not appreciably oxidized by the support is in line with the relatively high air stability of this complex when compared to the anion.

Infrared measurements have shown that the heteronuclear noble metal cluster complexes remain intact on a dehydrated Al$_2$O$_3$ surface. Upon air exposure the cluster complexes generally undergo rapid decomposition. This process is probably irreversible. When subjected to hydrogen reduction the organic portion of the cluster complexes is destroyed, leaving behind reduced heteronuclear noble metal clusters on the Al$_2$O$_3$ surface. This novel method of catalyst preparation offers several potential advantages. Alloy formation on the Al$_2$O$_3$ surface by the above procedure may be more favorable than by the conventional coimpregnation of monomeric, aqueous salt solutions. In the latter case good contacting between the supported metal atoms requires that both metal salts are equivalently adsorbed by the Al$_2$O$_3$ support. This situation is known not to be generally obeyed. Metal-support interactions may, in some cases, drive heterometallic systems into a state where the metals approach monoatomic dispersion. Well dispersed metal phases, as is often found in low metal-loaded (<1%) catalysts, may disfavor surface alloy formation. The covalent metal-metal bonds present in heteronuclear noble metal cluster complexes may, in contrast, maintain the heteroatoms within bonding distance as the molecular complex is decomposed on the $Al_2O_3$ surface. In essence, a supported bimetallic cluster complex may reduce as a single molecular entity, whereas, two supported monomeric salts would possess different reduction characteristics. The latter case could result in metallic phase separation. The decomposition of a heteronuclear noble metal cluster complex may also generate discrete heteronuclear crystallites on the support surface. We suggest that the reductive decomposition of a $PtIr_6$ cluster complex may yield uniform, three-dimensional metal clusters within which the basic octahedral symmetry of the starting complex is retained. The conventional coimpregnation of monomeric Pt and Ir salts in a 1 to 6 mole ratio would not be expected to generate a discrete three-dimensional, 1 to 6 clustering of Pt and Ir atoms. Available evidence suggests that well dispersed $Pt/Al_2O_3$ catalysts possess pseudo two-dimensional (pill-box) crystallites. The Pt crystallites are flat and of uniform thickness on the $Al_2O_3$ surface. Three-dimensional crystallites proposed to be present in heteronuclear cluster catalysts would possess a relatively higher number of unsaturated atoms than a pill-box cluster of metal atoms. The presence of unsaturated metal atoms would be predicted to modify catalytic reaction patterns. An a priori statement as to the direction of catalyst modification (activity and/or selectivity) cannot, however, be made with any certainty.

Hydrogen Chemisorption Studies

Selected supported Pt/Ir catalysts were subjected to hydrogen chemisorption measurements. The apparatus used for adsorption measurements of supported catalysts was a conventional glass vacuum system. A high precision, fused quartz Bourdon pressure gauge manufactured by Texas Instrument Company, Houston, Tex., was used for the $H_2$ adsorption measurements. Prior to adsorption measurements the catalysts were reduced in situ under flowing hydrogen (ca. 500 cc/min) for 2.0 hours at 750°–930° F. In some cases argon BET surface areas were also determined. The dispersions of standard and cluster deposited Pt/Ir catalysts, as measured by their characteristic H/M values, are compared in Table VI.

The standard catalysts (prepared with standardized $H_2MCl_6$ acid (M=Ir or Pt) solutions) were found to display H/M ratios greater than unity. The departure from unity was found to be greater in the more dilute catalysts (compare catalysts 1 and 2). We assume that these high H/M ratios indicate complete dispersion of the supported metal phases. We further assume that hydrogen uptake in excess of that corresponding to an H/M=1 is associated with either hydrogen spillover or multiple hydrogen bonding to the metal crystallites. The method of impregnation, either incipient wetness or adsorption from an overstanding solution, did not measurably alter the H/M ratios of the standard catalysts.

Supported cluster complex catalysts were in most cases found to display H/M ratios near unity. The most serious departure from this value was found in the case of a higher loaded catalyst (catalyst 8) which exhibited an H/M ratio of 0.80. The apparent absence of hydrogen spillover or multiple hydrogen bonding in supported heteronuclear noble metal cluster catalysts is not understood. We have assumed, however, that the metal phases in these catalysts are generally well dispersed. As was found for the standard catalysts, the mode of impregnation did not measurably affect the dispersion level of the supported heteronuclear noble metal cluster catalysts. The presence of chloride was also found not to have an affect on the dispersion level of the cluster catalysts of the instant invention.

Reduced $PtIr_6$ and $PtIr_2$ cluster catalysts were generally found to exhibit H/M ratios of near 1.0. The metallic phases present in these catalysts were completely amorphous to X-ray diffraction measurement. Standard Pt/Ir catalysts containing comparable metal loadings were found to display H/M ratios between 1.5 and 1.8. The uptake of hydrogen in excess of H/M=1.0 was assumed to be due to either hydrogen spillover onto the $Al_2O_3$ support or to multiple hydrogen bonding to the crystallites. The absence of hydrogen spillover or multiple hydrogen bonding in Pt-Ir cluster catalysts is not understood. The dissimilar hydrogen adsorption capacities may reflect crystallite and/or metal-support interaction differences between standard and cluster Pt-Ir catalysts. For catalytic purposes we consider both the standard and cluster catalysts to be fully dispersed.

C. Hydrocarbon Conversion Reactions

Hydrocarbon conversion reactions were carried out in a 25 cc stainless-steel, fixed-bed, isothermal hydrotreating unit. The unit was operated in a single pass mode. Hydrogen was passed through deoxo and molecular sieve drying units prior to use. The hydrotreating unit is heated by a fluidized sand bath. The feed is delivered by a dual barrel Ruska Pump which allows continuous operation. Model compound reaction products were analyzed by in-line G.C. measurements. Gas chromatographic measurements were carried out in a Perkin-Elmer 990 Chromatograph using flame ionization detection. The column was ⅛ inch by 30 feet packed with a 20% SP-2100 substrate on a ceramic support.

n-Heptane dehydrocyclization experiments were carried out on unsulfided catalysts at 900° F. under 200 psig total pressure. A w/hr/w of 20 was employed. The $H_2$/n-$C_7$ mole ratio was maintained at a 5.0–5.6 level. Under these conditions n-heptane is converted into 21–23 products, starting with methane and extending through the isomeric xylenes. Experiments were typically carried out for 100–200 hours.

Naphtha reforming experiments were carried out at 905°–912° F. under 200 psig total pressure. A w/hr/w of 2.26 was employed. Hydrogen was supplied at a 6000 SCF $H_2$/bbl level. In situ reduced catalysts (930° F., $H_2$ (1150 cc/min), 2.0 hours), were sulfided to breakthrough with 0.5% $H_2S/H_2$ (1.0 atm) at 700° F. The reformate was collected over ice and was analyzed for research octane number (RON). Off gases were monitored by wet test meter. Catalysts were typically maintained on feed for 200–300 hours. Relative catalysts activities (RCA) were calculated using equation 3:

$$RCA = \frac{(100)(S.V.)}{(Q_B)(T_B)} \quad (3)$$

where S.V.=space velocity and $Q_B$ and $T_B$ are empirical pilot plant correlations of the octane effect and temperature effect, respectively.

Spent catalysts from the above hydrocarbon conversion reactions were routinely analyzed for % carbon and % chlorine.

n-Heptane Dehydrocyclization Results

Screening studies singled out $PtIr_6$ cluster catalysts as being of particular interest for catalytic reforming. The results of n-heptane dehydrocyclization experiments carried out over 0.4% Ir/0.067%Pt/0.47%Cl/Al$_2$O$_3$ catalysts are presented in Table V. A supported PtIr$_6$ cluster catalyst with added chloride is compared against a standard catalyst of the same nominal metals and chloride concentrations. The catalysts were maintained on feed for 210 hours so as to compare their reactivation rates. Catalysts activity was allowed to decline with time on feed (no temperature or space velocity corrections were made to maintain a constant conversion level). This mode of operation allows one to determine relative deactivation rates.

Figure 6:
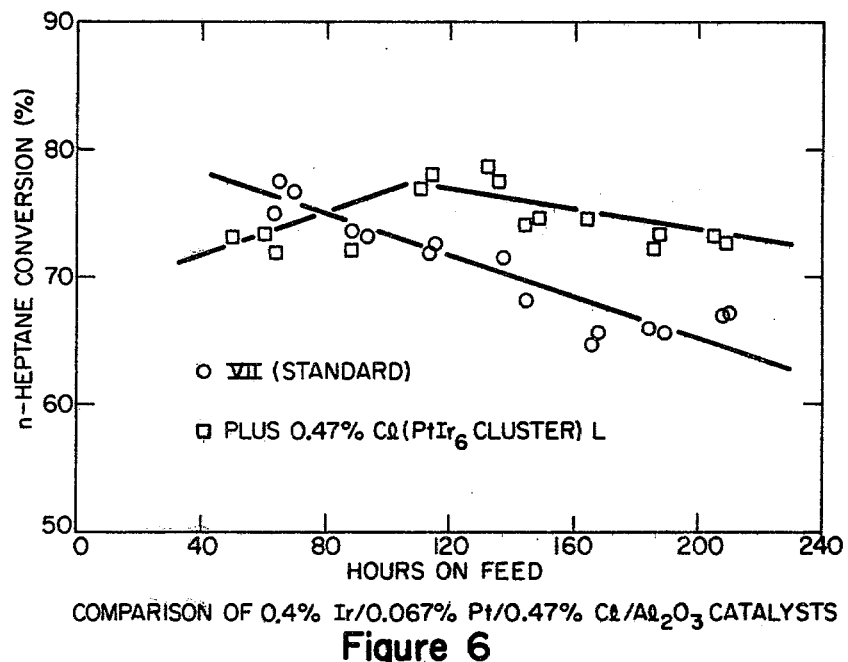
FIGS. 6-14 are graphs illustrating and comparing the activity, conversion and selectivity of catalysts of this invention with catalysts made using standard techniques known to those skilled in the art.
Figure 7:
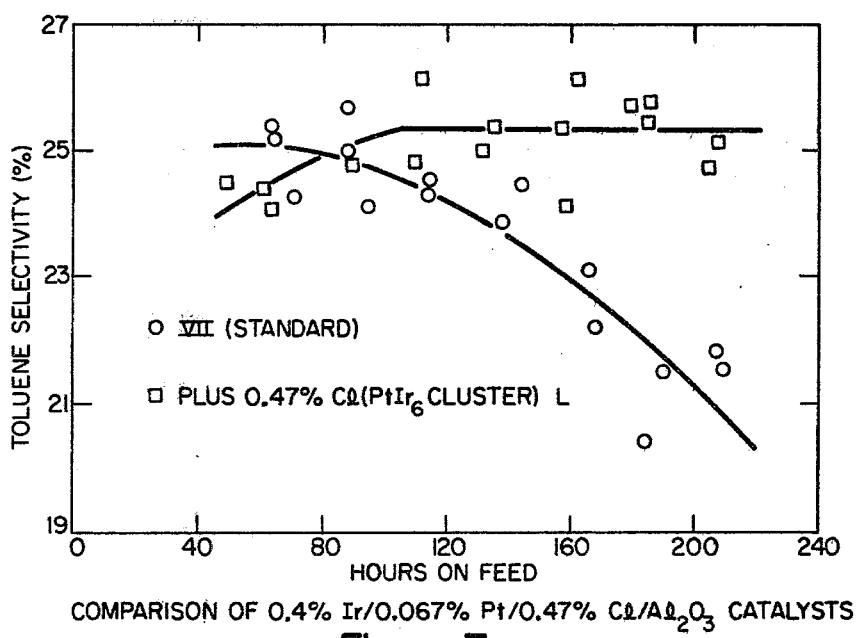
Figure 8:
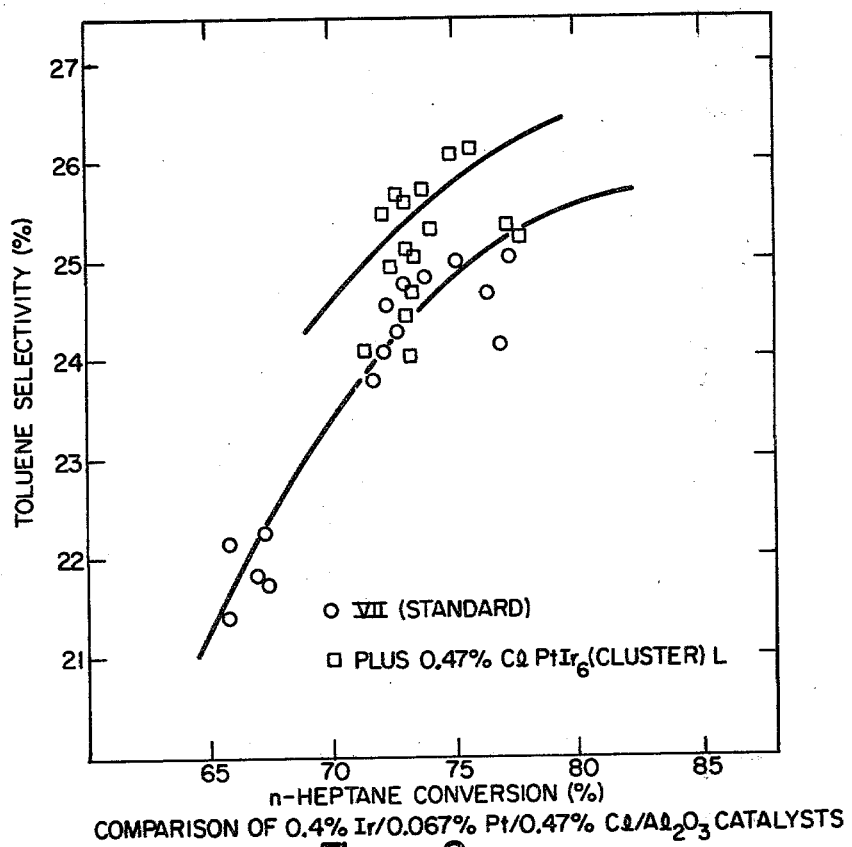
Figure 9:
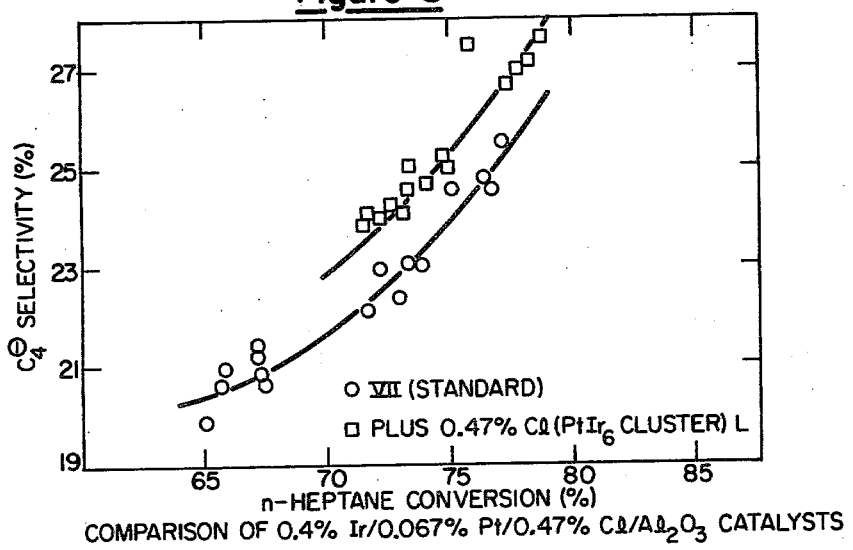
Figure 10:
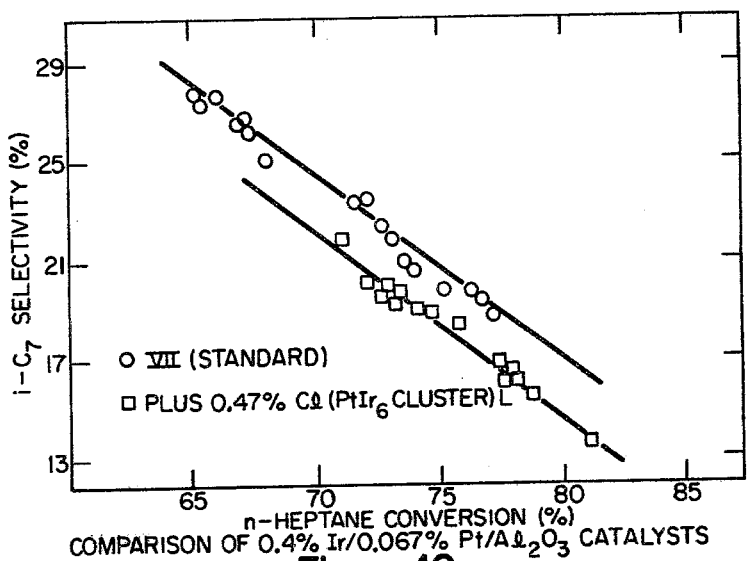

The decline in n-heptane conversion with time on feed is shown in FIG. 6. This plot clearly shows that under identical reaction conditions the PtIr$_6$ cluster complex maintains a significantly higher level of conversion than the standard catalyst. Toluene selectivity as a function of time curves are shown in FIG. 7. For lined out catalysts, between 100 and 200 hours on feed, the cluster catalyst displayed a constant selectivity to toluene of about 25%. During the same time period, however, the standard catalyst experienced about a 4% decline in toluene selectivity. Toluene selectivity as a function of n-heptane conversion curves are shown in FIG. 8. At n-heptane conversions between 70 and 77% the cluster catalyst consistently exhibits a higher (0.5–1.0%) toluene selectivity than the standard catalyst. FIGS. 9 and 10 are plots of C$_4^\ominus$ selectivity and i-C$_7$ selectivity versus n-heptane conversion, respectively. The PtIr$_6$ cluster catalyst was found to exhibit about a 1.5% higher selectivity to C$_4^\ominus$ products (at a given conversion level) than the standard catalyst. To counterbalance the higher toluene and C$_4^\ominus$ selectivities the PtIr$_6$ cluster catalyst demonstrated about a 2% lower i-C$_7$ isomerization selectivity than the standard catalyst. The spent PtIr$_6$ cluster and standard catalysts were found to contain 0.7 and 1.2% coke, respectively.

In an effort to understand the effect of cluster size on hydrocarbon conversion reactions, several 0.32% Ir/0.16% Pt catalysts were prepared by depositing (pyridine)$_2$Pt[Ir$_2$(CO)$_7$] onto Al$_2$O$_3$. The chloride level was adjusted to 0.5% by the addition of aqueous HCl to a reduced PtIr$_2$ cluster catalyst. The results of n-heptane dehydrocyclization over a series of 1:2 Pt-Ir catalysts are compared in Table VI. The activity of a chlorided PtIr$_2$ cluster catalyst was found to be nearly the same as a standard catalyst. The chloride-free cluster catalyst was somewhat less active (~5% lower conversion) than the chloride containing catalysts. Throughout the lifetime of the runs the cluster catalysts exhibited higher C$_4^\ominus$ selectivities (5–6%) than the standard catalyst. The PtIr$_2$ cluster catalysts were found to be less active isomerization catalysts than the standard catalyst. Within experimental error, the three 1:2 Pt-Ir catalysts exhibited equivalent selectivities to toluene. After 100 hours on feed the catalysts produced nearly equivalent amounts of coke.

A (pyridine)$_3$Pt[Ru$_3$(CO)$_{12}$] on Al$_2$O$_3$ catalyst (nominally 0.33% Ru/0.22% Pt) was prepared. The results of n-heptane dehydrocyclization experiments over this catalyst are presented in Table VII. The PtRu$_3$ cluster catalyst was found to be considerably less active than a comparably loaded standard Pt/Ir catalyst. The catalyst demonstrated extremely high C$_4^\ominus$ and i-C$_7$ selectivities. A very poor toluene selectivity was shown by the catalyst and did not markedly improve upon increasing the temperature to 950° F. The overall selectivity pattern exhibited by the PtRu$_3$ cluster catalyst appears to be governed by the high hydrogenolysis activity of the Ru component.

n-Heptane Reaction Patterns

Alumina supported PtIr$_6$ cluster catalysts were found to exhibit markedly different n-heptane dehydrocyclization reaction patterns than conventionally prepared 1:6 Pt-Ir catalysts (see Table V). A PtIr$_6$ cluster catalyst in which the acidity level was balanced by the addition of chloride ion was found to be considerably more active than a standard catalyst (see FIG. 6). The activity advantage may result in part from a lower coke level on the PtIr$_6$ cluster catalyst. The lower coke make found with PtIr$_6$ cluster catalysts suggests that the useful lifetimes of these catalysts are substantially longer than standard Pt-Ir catalysts.

Under normal reforming conditions the dehydrocyclization of n-heptane produces a complex mixture of reaction products. These products can be conveniently divided into three groups (equation 4):

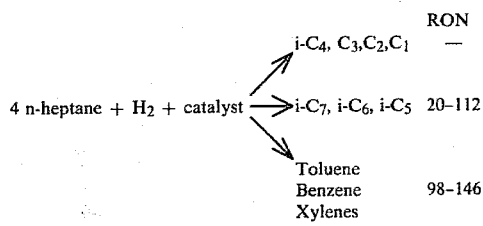

Of these products, toluene, benzene and the isomeric xylenes are the most desirable because of their high research octane numbers (RON) and their use as gasoline blending agents. The C$_4^\ominus$ yield is to be minimized as these products represent feed losses. The C$_5^\oplus$ skeletal isomerization products are in general product credits as they possess considerably higher RON values than n-heptane. Under typical reforming conditions it has been found that product selectivities are not greatly influenced by catalyst acidity. The activity (as measured by n-heptane conversion) of cluster catalysts was, however, increased upon the addition of chloride ion.

The dehydrocyclization and isomerization of n-heptane are considered by numerous workers in the field to be dependent upon the dispersion of the metal component. In this sense these reactions can be considered to be demanding. The selectivity patterns exhibited by a chlorided PtIr$_6$ cluster catalyst were found to be substantially different than those exhibited by a standard 1:6 Pt-Ir catalyst containing an equivalent chloride level. Toluene selectivity as a function of time over these catalysts are presented in FIG. 7. As previously stated, between 100 and 200 hours on feed the PtIr$_6$ cluster catalyst displayed a constant toluene selectivity of about 25%. Throughout the lifetime of the run the standard catalyst experienced about a 4% decline in toluene selectivity. These results indicate that, in contrast to the standard catalyst, the PtIr$_6$ cluster catalyst maintained a constant toluene selectivity as conversion decreases. At n-heptane conversion levels between 70–77% the PtIr$_6$ cluster catalyst demonstrated a consistently higher (~1%) toluene selectivity (see FIG. 8). At comparable conversion levels the PtIr$_6$ cluster catalyst produced a 1.5% higher C$_4^\ominus$ selectivity than the standard catalyst (see FIG. 9). The standard catalyst was found to exhibit about a 2.0% higher selectivity to i-C$_7$ products than the PtIr$_6$ cluster catalyst (see FIG. 10). The hydrocracking and isomerization selectivity differences shown by the standard and PtIr$_6$ cluster catalysts suggest that the metal crystallites are on the average smaller in the case of the standard catalyst since it is known that hydrocracking decreases and isomerization increases (for C$_5$ to C$_7$ paraffins) as the dispersion of Pt/Al$_2$O$_3$ catalysts increases. The higher H/M ratios exhibited by standard Pt-Ir catalysts also suggest that these catalysts have smaller particles (fewer metal atoms in each crystallite) than the Pt-Ir cluster catalysts.

The enhanced dehydrocyclization selectivity demonstrated by the PtIr$_6$ cluster catalyst cannot, however, be completely correlated with a simple metal crystallite size (dispersion) argument. The dehydrocyclization selectivity differences may be due to subtle changes in crystallite geometries. The PtIr$_6$ cluster catalyst may contain small (11 Å crystallites based upon H/M values of around 1.0) three-dimensional, bimetallic clusters while the standard catalysts (H/M=1.5–1.8) may contain smaller (less than 10 Å) two-dimensional bimetallic clusters. These proposed microstructure differences can be used to rationalize the dehydrocyclization advantage displayed by the PtIr$_6$ cluster catalyst. The presence of small three-dimensional clusters, as opposed to still smaller two-dimensional clusters, would favor dehydrocyclization since carbocyclic reaction intermediates would be preferentially generated on a less highly coordinated three-dimensional bimetallic cluster. Even though PtIr$_6$ cluster and standard 1:6 Pt-Ir catalysts are essentially 100% dispersed the cluster crystallite geometry and hence catalytic specificity exhibited by the two catalysts are markedly different.

Alumina supported PtIr$_2$ cluster catalysts were prepared in an attempt to ascertain if the size of the precursor heteronuclear cluster complex could influence hydrocarbon conversion reactions. For n-heptane dehydrocyclization PtIr$_2$ cluster catalysts (chlorided and chloride free) were found to produce substantially higher C$_4\ominus$ selectivities than a standard 1:2 Pt-Ir catalyst (see Table VI). At comparable conversion levels this C$_4\ominus$ selectivity debit amounted to about 5–6%. The high hydrocracking activity demonstrated by the chloride-free PtIr$_2$ cluster catalyst was not anticipated. This result suggests that the C$_4\ominus$ products are generated primarily over metal sites (the quantity of support acid cracking is small). The mechanism whereby the metal clusters present on the PtIr$_2$ cluster catalysts produce higher gas makes than the standard catalyst is not known. As expected the activity of a PtIr$_2$ cluster catalyst was increased (~5%) by the addition of chloride ion. The n-heptane conversion level of a chlorided PtIr$_2$ cluster catalyst was found to be comparable with that of the standard catalyst. Both PtIr$_2$ cluster catalysts demonstrated lower (6–7%) isomerization selectivities than the standard catalyst. These results cannot be correlated with catalyst acidity differences since the chlorided PtIr$_2$ cluster and standard catalyst contain nearly the same chloride concentrations. The higher hydrocracking and lower isomerization selectivities demonstrated by the PtIr$_2$ cluster catalysts suggest (as for the PtIr$_6$ cluster catalyst) that the average metal crystallite size is somewhat larger in these catalysts than in the standard catalyst. Within experimental error the three 1:2 Pt-Ir catalysts demonstrated equivalent toluene selectivities. The spent catalysts were found to produce nearly the same amounts of coke.

The precursor PtIr$_2$ cluster complex is most probably square-planar and may upon deposition and reduction on an Al$_2$O$_3$ surface yield a two-dimensional (raft-like) clustering at Pt and Ir atoms. The simultaneous impregnation of Al$_2$O$_3$ with a 2:1 mixture of Ir and Pt acid solutions may produce upon reduction structurally similar bimetallic sites. If the above process were in fact to occur during catalyst preparation the similar catalytic patterns (activity, toluene selectivity, coke make) shown by PtIr$_2$ cluster and standard 1:2 Pt-Ir catalysts can be rationalized.

The toluene selectivities exhibited a PtIr$_6$ cluster catalyst were found to be 5 to 7% higher than a PtIr$_2$ cluster catalyst (see Tables V and VI). The dehydrocyclization selectivity advantage demonstrated by the PtIr$_6$ cluster catalyst is too large to be accounted for by either the difference in Ir content or conversion level. Since the PtIr$_6$ and PtIr$_2$ cluster catalysts are both 100% dispersed the activity and dehydrocyclization selectivity advantage exhibited by the PtIr$_6$ cluster catalyst must reflect subtle differences in catalyst microstructure. Different supported microstructures can be rationalized if we assume that deposition of a PtIr$_6$ cluster complex generates a three-dimensional bimetallic cluster while a PtIr$_2$ cluster complex yields a two-dimensional bimetallic cluster. As discussed earlier, three-dimensional clusters should more readily catalyze the dehydrocyclization of n-heptane than two-dimensional clusters.

A reduced PtRu$_3$ cluster complex on Al$_2$O$_3$ catalyst was found to be considerably less active for n-heptane dehydrocyclization than a comparably loaded Pt/Ir catalyst (see Table VII). The PtRu$_3$ cluster catalyst demonstrated high C$_4\ominus$ and i-C$_7$ selectivities. A very low toluene selectivity was shown by the catalyst and this did not improve significantly upon increasing the reaction temperature from 900° to 950° F. The overall selectivity pattern exhibited by the PtRu$_3$ cluster catalyst appears to be governed by the high hydrogenolysis activity of the Ru component. At comparable n-heptane conversion levels a Pt only catalyst (0.3% Pt/0.6% Cl) would exhibit C$_4\ominus$ and toluene selectivities of 10 and 15%, respectively. The poor activity and selectivity pattern displayed by the PtRu$_3$ cluster catalyst indicated that such catalysts would not likely prove to be useful in catalytic reforming applications, but would be useful hydrogenation catalysts.

Naphtha Reforming Results

The above n-heptane dehydrocyclization experiments have shown that several Pt-Ir noble metal cluster catalysts exhibit modified reaction patterns when compared to conventionally prepared Pt-Ir bimetallic catalysts.

The modified n-heptane reaction patterns displayed by noble metal cluster catalysts has been tentatively ascribed to the generation of unique Pt-Ir clusters on the Al$_2$O$_3$ support surface. Such unique heterometallic clusters significantly alter reactions dependent upon catalyst microstructure (demanding reactions). These results suggest that Pt-Ir cluster catalysts may find particular application in catalytic reforming.

1:6 Pt-Ir Catalysts

The results of naphtha reforming over Al$_2$O$_3$-supported PtIr$_6$ and conventional 1:6 Pt:Ir catalysts (nominally 0.4% Ir/0.067% Pt/0.7% Cl) are presented in Table VIII. The conventional 1:6 Pt-Ir catalyst was in the form of 1/16 inch extrudate while the PtIr$_6$ cluster was in the form of 10/20 mesh. After 170 hours on feed the standard catalyst was found to line out at a relative catalyst activity (RCA) of about 190. The PtIr$_6$ cluster catalyst (prepared by depositing (Py)$_2$Pt[Ir$_6$(CO)$_{15}$] on $\eta$-Al$_2$O$_3$) lined out at a RCA near 410. Thus, under the same set of reaction conditions the PtIr$_6$ cluster catalyst is at least 2.2 times more active than the conventional catalyst. The spent catalysts were found to contain essentially the same chloride loadings. The PtIr$_6$ cluster catalyst demonstrated a 30% lower coking rate than the conventional catalyst.

In an attempt to eliminate diffusional effects, which might account in part for the large naphtha reforming activity difference, PtIr$_6$ cluster and conventional catalysts were prepared on 1/16 inch Al$_2$O$_3$ extrudate. The results of naphtha reforming over these catalysts are presented in Table IX. The RCA patterns exhibited by the conventional and PtIr$_6$ cluster catalysts were found to be in good agreement with those of the previous runs. After about 170 hours on feed the PtIr$_6$ cluster catalyst was found to be about 2.4 times more active for naphtha reforming than the conventional catalyst. After the same length of time on feed the activity difference found in the previous runs was close to 2.2. These results suggest that the form of a PtIr$_6$ cluster catalyst (1/16 inch extrudate or 10/20 mesh) does not measurably effect its activity. Also, the type of Al$_2$O$_3$ ($\eta$ or $\gamma$) had no apparent effect on catalyst performance.

Ir Only Catalysts

Several 0.4% Ir/0.7% Cl/Al$_2$O$_3$ catalysts were prepared in an attempt to ascertain what contribution the Pt component had on naphtha reforming over 1:6 Pt-Ir catalysts. A Ir$_6$ cluster catalyst was prepared by depositing a [(C$_2$H$_5$)$_4$N]$_2$[Ir$_6$(CO)$_{15}$] cluster complex on $\eta$-Al$_2$O$_3$. The results of naphtha reforming over Ir$_6$ cluster and conventional catalysts are presented in Table X. For the first 120 hours on feed the Ir$_6$ cluster and conventional catalysts exhibited nearly comparable naphtha reforming activities. After this period, the activity of the Ir$_6$ cluster catalyst rapidly declined reaching a RCA value of around 60 after 200 hours on feed. The spent catalysts were found to have comparable coke and chloride contents. Thus the rapid fall off in activity displayed by the Ir$_6$ cluster catalyst cannot be explained by either a large coke make or chloride loss. At about 160 hours on feed the activity of the Ir$_6$ cluster catalyst was only about 30% as great as that of a PtIr$_6$ cluster catalyst. The large activity advantage demonstrated by the PtIr$_6$ cluster catalyst cannot be accounted for by the presence of the platinum component. After about 160 hours on feed the conventional 0.4% Ir catalyst was found to be about 1.4 times more active for naphtha reforming than a conventional 0.4% Ir/0.06% Pt catalyst.

Composite RCA versus time on feed curves for the catalysts summarized in Tables VIII, IX and X are shown in FIG. XI. These curves demonstrate that the activity patterns exhibited by conventional and PtIr$_6$ cluster catalysts are very reproducible. The curve displayed by the PtIr$_6$ cluster catalysts clearly shows a 1.6 fold increase in activity between 60 and 120 hours on feed. This behavior is likely associated with a gradual loss of sulfur. After about 140 hours on feed both the conventional and PtIr$_6$ cluster catalysts exhibited lined out activities.

The nearly 2.4 fold activity advantage demonstrated by the PtIr$_6$ cluster catalyst is significant. Since the metal and chloride content of the conventional and PtIr$_6$ cluster catalysts are equivalent, the enhanced reforming activity demonstrated by the PtIr$_6$ cluster catalyst must be related to differences in catalyst microstructure (heterometallic cluster geometries).

Figure 12:
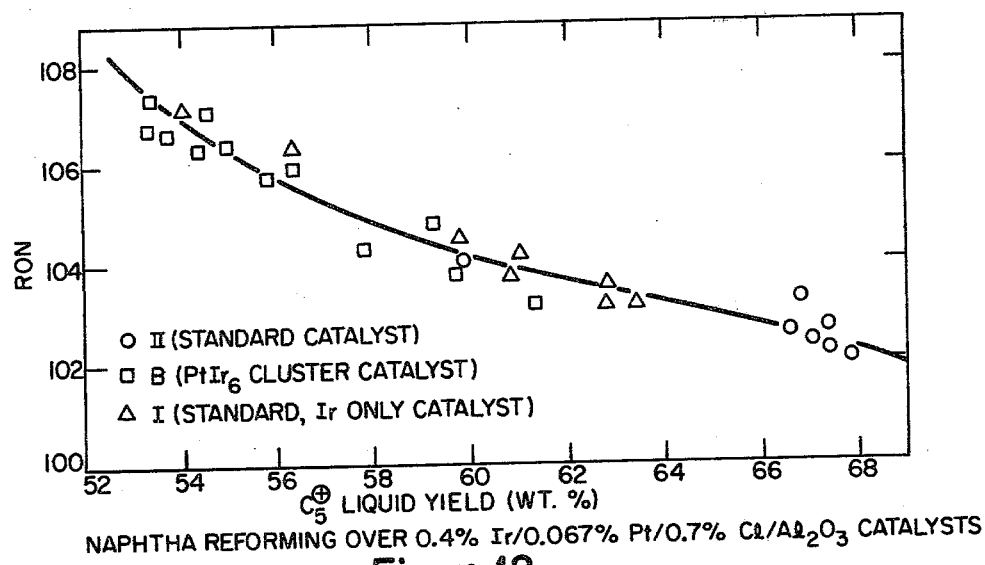

During the catalytic runs outlined in Tables VIII, IX and X the C$_5$⊕ fraction was collected over ice and weighed. From this weight, a % weight yield was calculated from a knowledge of the weight of feed employed during time collection periods. FIG. 12 presents curves of research octane number (RON) versus C$_5$⊕ liquid yield (wt.%) for the catalysts listed in Tables VIII, IX and X. At comparable RON values the conventional and PtIr$_6$ cluster catalysts demonstrate similar C$_5$⊕ liquid yield.

1:2 Pt-Ir Catalysts

Figure 13:
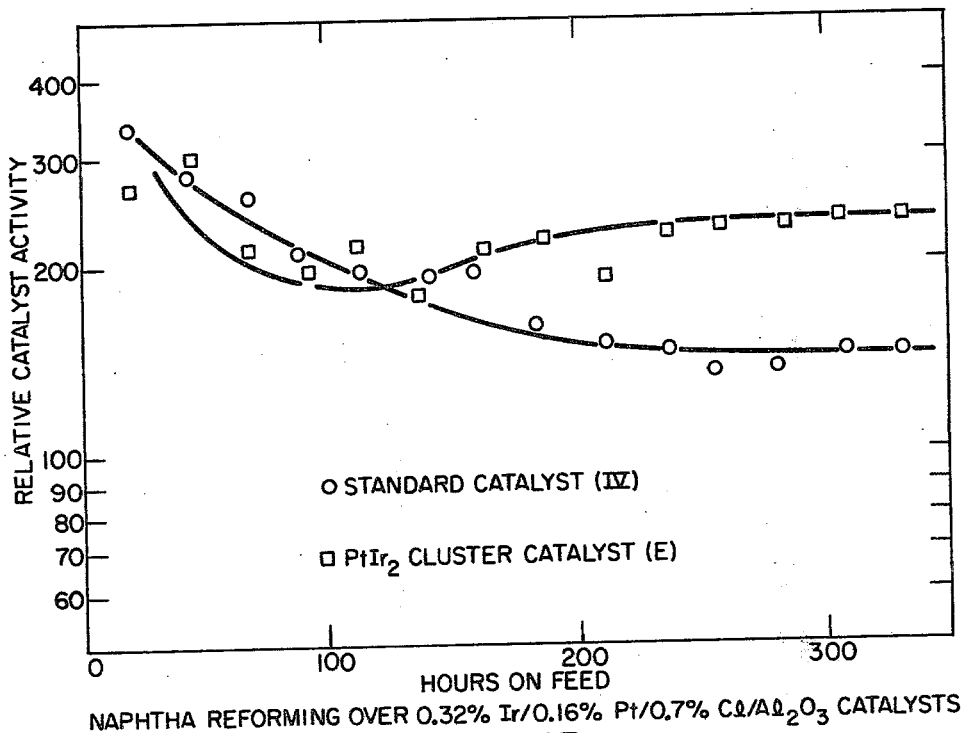
Figure 14:
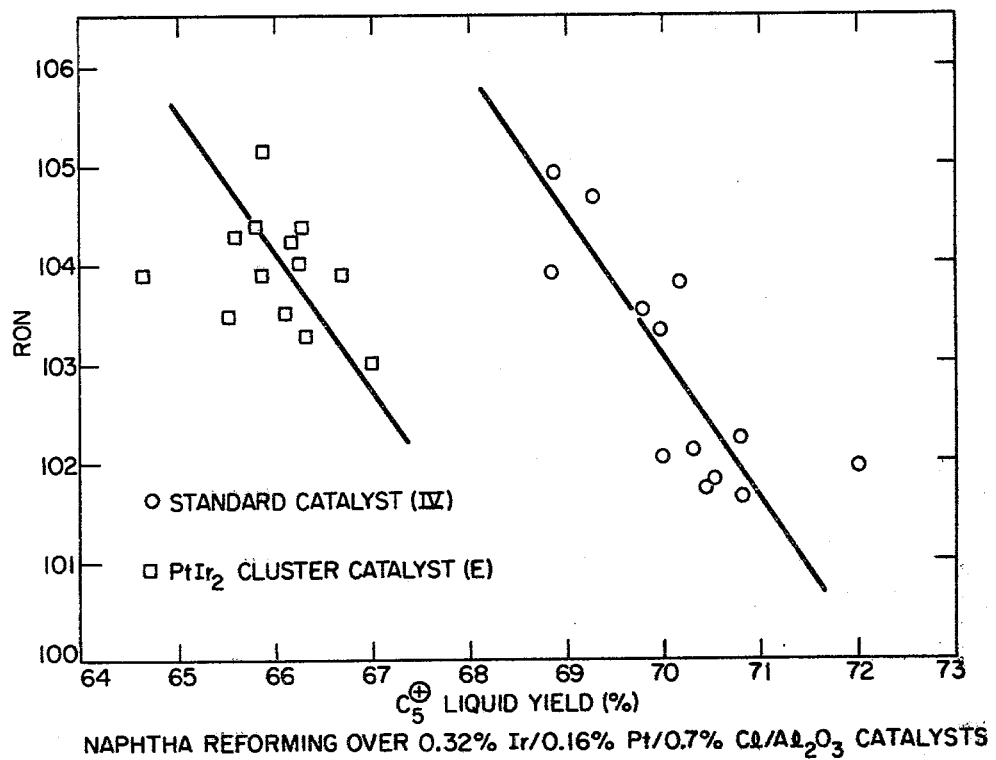

The results of naphtha reforming over 0.32% Ir/0.16% Pt/0.7% Cl/Al$_2$O$_3$ are summarized in Table XI. The PtIr$_2$ cluster catalyst was prepared by depositing a (Py)$_2$Pt[Ir$_2$(CO)$_7$] cluster complex on $\eta$-Al$_2$O$_3$. Both the conventional 1:2 Pt-Ir and PtIr$_2$ cluster catalysts were in the form of 10/20 mesh. Curves of RCA versus time on feed are shown in FIG. 13. After about 200 hours on feed the PtIr$_2$ cluster catalyst was found to be about 1.6 times more active for naphtha reforming than the conventional 1:2 Pt-Ir catalyst. The spent catalysts were found to display similar chloride levels. The spent PtIr$_2$ cluster catalyst contained a slightly higher coke content than the conventional catalyst. FIG. 14 presents curves of RON versus C$_5$⊕ liquid yield (wt%) for the conventional and PtIr$_2$ cluster catalysts listed in Table XI. At a given RON value the conventional catalyst demonstrated about a 3% higher C$_5$⊕ liquid yield than the PtIr$_2$ cluster catalyst. The liquid yield advantage exhibited by the conventional catalyst is significant. The higher naphtha cracking activity displayed by the PtIr$_2$ cluster catalyst is in good agreement with the higher C$_4$⊕ selectivity demonstrated by this catalyst for n-heptane dehydrocyclization. Since the conventional and PtIr$_2$ cluster catalysts contain the same metal and chloride concentration, the higher activity and enhanced cracking activity shown by the PtIr$_2$ cluster catalyst must be related to differences in catalyst microstructure.

Catalytic Reforming Over 1:6 Pt-Ir Catalysts

Figure 11:
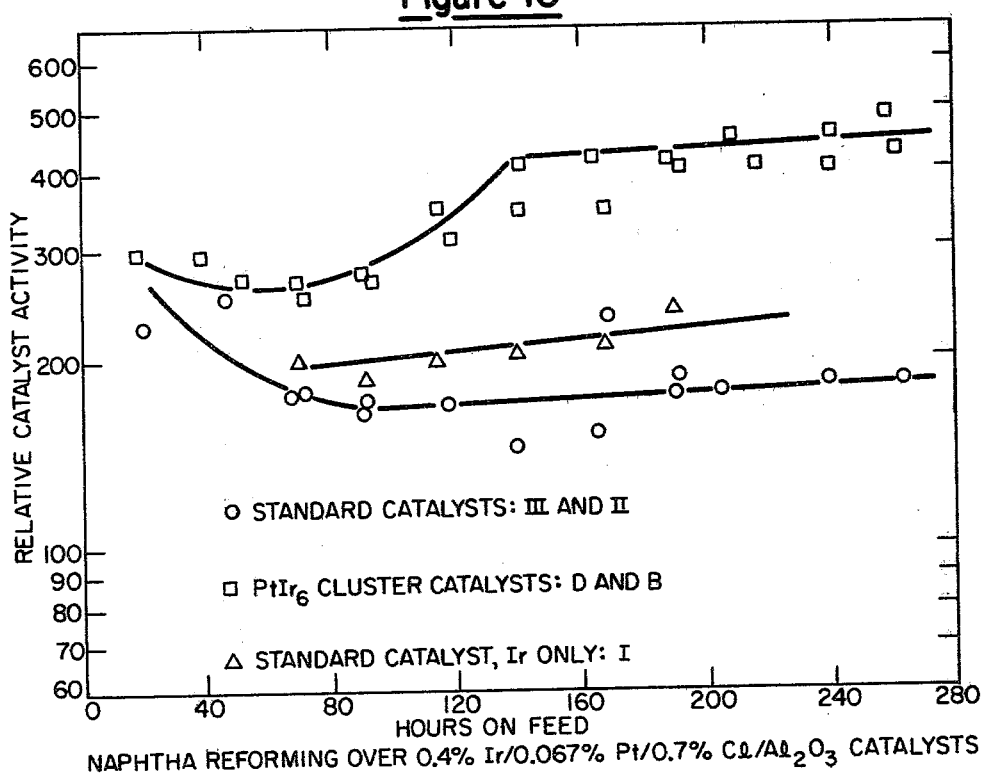

Naphtha reforming patterns over 0.4% Ir/0.067%-Pt/0.7% Cl/Al$_2$O$_3$ catalysts are presented in Tables VIII and IX. The activity patterns were found to be quite reproducible from preparation to preparation. The PtIr$_6$ cluster catalyst data indicate that no measurable catalytic effect is produced upon changing from 10/20 mesh to 1/16 inch extrudate catalyst particles. A lined out PtIr$_6$ cluster catalyst was found to be at least 2.4 times more active for naphtha reforming than a conventional 1:6 Pt-Ir catalyst (see FIG. 11). The composite RCA versus time curve exhibited by the PtIr$_6$ cluster catalyst clearly shows an increase in activity between 60 and 120 hours on feed. This behavior has been ascribed to the gradual loss of sulfur from the catalyst. After about 140 hours on feed the conventional and PtIr$_6$ cluster catalysts maintain fairly flat activity curves. These activity plateaus suggest that the catalysts have reached a steady state sulfur concentration. The shape of the PtIr$_6$ cluster catalyst curve further suggests that this catalyst may be able to tolerate feedstocks containing higher sulfur contents. Since the spent catalysts were found to contain nearly equivalent chloride contents, the large activity advantage exhibited by the PtIr$_6$ cluster catalyst cannot be correlated with a catalyst acidity difference. The activity advantage must reflect differences in catalyst microstructure. The bimetallic clusters present in the PtIr$_6$ cluster catalyst appear to be better suited to aromatize a naphtha feedstock.

The suggested enhanced aromatization activity implies that the PtIr$_6$ cluster catalyst is intrinsically more efficient in carrying out demanding dehydrocyclization transformations. The higher toluene selectivity demonstrated by the PtIr$_6$ cluster catalyst (compared to a conventional 1:6 Pt-Ir catalyst) for n-heptane dehydrocyclization lends credence to this argument. The 30% lower coking rate displayed by the PtIr$_6$ cluster catalyst suggests that its useful lifetime will be considerably longer than the conventional catalyst.

As the activity of reforming catalysts increases, the yield of C$_5$⊕ reformate generally decreases. The decreased C$_5$⊕ liquid yield is the direct result of a higher cracking activity. During the catalytic reforming runs summarized in Tables VIII and IX the C$_5$⊕ liquid yield was monitored. FIG. 12 compares curves of RON versus C$_5$⊕ liquid yield (wt%) for PtIr$_6$ cluster and conventional 1:6 Pt-Ir catalysts. At a given RON value the conventional and PtIr$_6$ cluster catalysts appear to produce equivalent C$_5$⊕ liquid yields. The curve clearly shows that C$_5$⊕ liquid yields are highly dependent upon RON values. Since the individual runs were carried out under nearly identical conditions, RON values are a direct measure of catalyst activity.

Catalytic Reforming Over 1:2 Pt-Ir Catalysts

The results of naphtha reforming over 0.32% Ir/0.16% Pt/0.7% Cl/Al$_2$O$_3$ catalysts are presented in Table XI. To minimize any diffusional effects both catalysts were in the form of 10/20 mesh particles. The conventional and PtIr$_2$ cluster catalysts were found to line out after about 200 hours on feed (see FIG. 13). The PtIr$_2$ cluster catalyst displayed at least a 1.6 fold activity advantage over the conventional 1:2 Pt-Ir catalyst. The increase in activity between 100 and 200 hours on feed exhibited by the PtIr$_2$ cluster catalyst may be associated with a gradual loss of sulfur from the catalyst. At a given RON value the conventional catalyst was found to produce about a 3% higher C$_5$⊕ liquid yield than the PtIr$_2$ cluster catalyst (see FIG. 14). The magnitude of the liquid yield advantage shown by the conventional catalyst is significant. The higher naphtha cracking activity demonstrated by the PtIr$_2$ cluster catalyst is in good agreement with the higher C$_4$⊕ selectivity exhibited by this catalyst in n-heptane conversion experiments. Since the conventional and PtIr$_2$ cluster catalysts contain similar metal and chloride loadings the enhanced cracking activity shown by the PtIr$_2$ cluster catalyst must somehow reflect different metal catalyzed hydrocracking activities. The relatively poor liquid yields obtained with a PtIr$_2$ cluster catalyst may be improved by using a higher sulfur content naphtha. Since the PtIr$_2$ cluster catalyst displays a 1.6 fold activity advantage over a conventional 1:2 Pt-Ir catalyst, it is possible to use a higher sulfur level without seriously decreasing the activity edge.

Summary of Naphtha Reforming Patterns

PtIr$_2$ and PtIr$_6$ cluster catalysts have been found to be at least 1.6 and 2.4 times more active for naphtha reforming than conventional 1:2 and 1:6 Pt-Ir catalysts, respectively. A PtIr$_6$ cluster catalyst was found to be 1.8 times more active than a PtIr$_2$ cluster catalyst. The activity advantage shown by the PtIr$_6$ cluster cannot be accounted for by the difference in Pt content. Liquid yields are comparable over PtIr$_6$ cluster and conventional 1:6 Pt-Ir catalysts. A PtIr$_2$ cluster catalyst was, however, found to produce a significantly lower (~3%) C$_5$⊕ yield than a conventional 1:2 Pt-Ir catalyst.

The higher naphtha reforming activities and liquid yield differences have been ascribed to the presence of unique heterometallic sites on cluster catalysts. These sites appear to be more efficient in carrying out aromatization reactions than those present on conventional Pt-Ir catalysts. The generation of such heteronuclear sites may only be possible by the use of preformed, heteronuclear noble metal cluster complexes as supported catalyst precursors. The significantly different catalytic reforming activities displayed by PtIr$_2$ and PtIr$_6$ cluster catalysts further suggests that catalysts can be radically altered by changing the stoichiometry and molecular structure of the precursor complexes.

TABLE I

INFRARED BANDS (cm$^{-1}$) IN THE CARBONYL STRETCHING REGION FOR Pt/Ir. Pt/Ru AND Rh/Ir CLUSTER COMPLEXES

| | Compound | Nujol Mull[a] | THE Solution[b] |
|---|---|---|---|
| 1. | (pyridine)$_2$Pt[Ir$_6$(CO)$_{15}$] | 2024 vs | 2044 m |
| | | 1976 vs | 2022 sh |
| | | 1949 sh | 2011 vs |
| | | 1730 s, br | 1987 sh |
| | | | 1975 vs. |
| | | | 1785 m |
| | | | 1733 m |
| | Na$_2$[Ir$_6$(CO)$_{15}$] | | 2041 sh |
| | | | 2014 sh |
| | | | 1965 vs |
| | | | 1930 sh |
| | | | 1783 m |
| | | | 1725 m |
| | [(C$_2$H$_5$)$_4$N]$_2$[Ir$_6$(CO)$_{15}$] | | 2020 sh |
| | | | 1970 s |
| | | | 1910 sh |
| | | | 1770 s |
| | | | 1745 s |
| 2. | (pyridine)$_2$Pt[Ir$_2$(CO)$_7$] | 2043 sh | 2035 sh |
| | | 2011 sh | 2009 sh |
| | | 1979 vs, br | 1983 vs |
| | | 1934 sh | 1938 sh |
| | | 1793 sh | 1785 sh |
| | | 1729 s | 1732 m-s |
| | Na[Ir(CO)$_4$] | | 1896 vs |
| | | | 1863 sh |
| 3. | [(C$_6$H$_5$)$_3$P]$_2$Pt[Ir(CO)$_3$P(C$_6$H$_5$)$_3$]$_2$ | 2014 sh | 2014 sh |
| | | 1996 sh | 1995 sh |
| | | 1964 vs | 1982 sh |
| | | 1944 sh | 1962 vs |
| | | 1902 m-s | 1934 sh |
| | | 1796 w | 1906 m-s |
| | | 1761 vw | 1800 w |
| | | | 1764 sh |
| | Na[Ir(CO)$_3$P(C$_6$H$_5$)$_3$] | | 1867 vs |
| | | | 1820 s |
| 4. | (pyridine)$_3$Pt[Ru$_3$(CO)$_{12}$] | | 2050 sh |
| | | | 1999 vs |
| | | | 1977 sh |
| | | | 1962 sh |
| | | | 1945 m |
| | | | 1804 vw, br |
| | | | 1763 w |
| | Na$_2$[Ru$_3$(CO)$_{12}$] | | 2033 w |
| | | | 1960 sh |
| | | | 1946 vs |
| | | | 1918 sh |
| | | | 1891 sh |
| | | | 1717 vw |
| | | | 1649 w |
| 5. | ((C$_6$H$_5$)$_3$P)$_2$Rh(CO)[Ir(CO)$_4$] | | 2042 w |
| | | | 1995 sh |
| | | | 1987 vs |
| | | | 1962 sh |
| | | | 1932 m |

[a]KBr salt plates.
[b]Matched 0.10 mm KBr solution cells.

TABLE II

ANALYSES OF SELECTED Al₂O₃-SUPPORTED CATALYSTS[a]

| Catalyst | Nominal Loading (%) Pt | Ir | Ru | Found (%) Pt | Ir | Ru |
|---|---|---|---|---|---|---|
| Standard Catalysts | | | | | | |
| I | — | 0.40 | — | — | 0.38 | — |
| II | 0.067 | 0.40 | — | 0.089 | 0.33 | — |
| III | 0.067 | 0.40 | — | 0.081 | 0.36 | — |
| IV | 0.16 | 0.32 | — | 0.17 | 0.31 | — |
| V | 0.19 | — | 0.30 | 0.18 | — | 0.03 |
| Heteronuclear Noble Metal Cluster Catalysts | | | | | | |
| A[b] | — | 0.40 | — | — | 0.37 | — |
| B[c] | 0.067 | 0.40 | — | 0.054 | 0.35 | — |
| C[c] | 0.067 | 0.40 | — | 0.034 | 0.38 | — |
| D[c] | 0.067 | 0.40 | — | 0.036 | 0.40 | — |
| E[d] | 0.16 | 0.32 | — | 0.20 | 0.32 | — |
| F[e] | 0.19 | — | 0.30 | 0.19 | — | 0.40 |

[a]Analyses performed by Analytical Information Division, Exxon Research and Engineering Company.
[b][(C₂H₅)₄N]₂[Ir₆(CO)₁₅] precursor
[c](C₅H₅N)₂Pt[Ir₆(CO)₁₅] precursor
[d](C₅H₅N)₂Pt[Ir₂(CO)₇] precursor
[e](C₅H₅N)₃Pt[Ru₃(CO)₁₂] precursor

TABLE III

INFRARED BANDS (cm⁻¹) IN THE CARBONYL STRETCHING REGION FOR Pt/Ir AND Pt/Ru CLUSTER COMPLEXES SUPPORTED ON ALUMINA

| Catalyst | Metals (Wt %)[a] | Precursors[b] | Carbonyl Bands[c] |
|---|---|---|---|
| 1. D | Ir (0.4) | Py₂Pt[Ir₆(CO)₁₅] | 2064 sh |
| | Pt (0.067) | | 2046 sh |
| | | | 2024 vs |
| | | | 2009 sh |
| | | | 1968 sh |
| | | | 1804 w-m |
| 2. A | Ir (0.4) | [(C₂H₅)₄N]₂[Ir₆(CO)₁₅] | 2014 s |
| | | | 1987 vs |
| | | | 1956 sh |
| | | | 1926 sh |
| | | | 1800 w |
| | | | 1770 w, br |
| 3. E | Ir (0.32) | Py₂Pt[Ir₂(CO)₇] | 2065 w |
| | Pt (0.16) | | 2018 sh |
| | | | 2007 vs |
| | | | 1979 sh |
| | | | 1966 sh |
| | | | 1798 w-m |
| | | | 1755 sh |
| 4. G | Ir (2.0) | K[Ir(CO)₄] | 2073 sh |
| | | | 2035 sh |
| | | | 1996 vs |
| | | | 1926 vs |
| | | | 1892 sh |
| | | | 1868 sh |
| 5. H | Ru (0.33) | Py₃Pt[Ru₃(CO)₁₂] | 2057 w |
| | Pt (0.22) | | 2001 vs |
| | | | 1979 sh |
| | | | 1954 sh |
| | | | 1800 w, br |
| 6. J | Ru(2.0) | K₂[Ru₃(CO)₁₂] | 2086 w |
| | | | 2029 sh |
| | | | 1997 vs, br |
| | | | 1954 sh |
| | | | 1860 w |
| | | | 1804 w |

[a]Nominal metal loadings
[b](Py) = pyridine
[c]Spectra recorded as nujol mulls between KBr salt plates.

TABLE IV

CHARACTERIZATION OF Pt/Ir/Al₂O₃ CATALYSTS: APPARENT ACTIVE METAL SURFACE AREAS

| Catalyst | Metals (Wt. %)[a] | Chlorine (Wt %) | Precursors | Impregnation[b] Method | H/M[c] |
|---|---|---|---|---|---|
| 1. VI | Ir (1.2) | 1.4 | H₂IrCl₆ | I.W. (H₂O) | 1.1 |
| | Pt (0.2) | | H₂PtCl₆ | | |
| 2. VII | Ir (0.4) | 0.47 | H₂IrCl₆ | I.W. (H₂O) | 1.6 |
| | Pt (0.067) | | H₂PtCl₆ | | |
| 3. III | Ir (0.4) | 0.70 | H₂IrCl₆ | ADS (H₂O) | 1.7 |
| | Pt (0.067) | | H₂PtCl₆ | | |
| 4. II | Ir (0.4) | 0.70 | H₂IrCl₆ | ADS (H₂O) | 1.8 |
| | Pt (0.067) | | H₂PtCl₆ | | |
| 5. I | Ir (0.4) | 0.70 | H₂IrCl₆ | ADS (H₂O) | 1.8 |
| 6. VIII | Ir (0.32) | 0.48 | H₂IrCl₆ | I.W. (H₂O) | 1.5 |
| | Pt (0.16) | | H₂PtCl₆ | | |
| 7. IV | Ir (0.32) | 0.70 | H₂IrCl₆ | I.W. (H₂O) | 1.7 |
| | Pt (0.16) | | | | |
| 8. K | Ir (1.2) | 0.0 | Py₂Pt[Ir₆(CO)₁₅] | I.W. (THF) | 0.80 |
| | Pt(0.2) | | | | |
| 9. L | Ir (0.4) | 0.0 | Py₂Pt[Ir₆(CO)₁₅] | I.W. (THF) | 0.90 |
| | Pt (0.067) | | | | |
| 10 D | Ir (0.4) | 0.70 | Py₂Pt[Ir₆(CO)₁₅] | I.W. (THF) | 1.0 |
| | Pt (0.067) | | | | |
| 11. C | Ir (0.4) | 0.70 | Py₂Pt[IR₆(CO)₁₅] | ADS (THF) | 1.1 |
| | Pt (0.067) | | | | |
| 12. B | Ir (0.4) | 0.70 | Py₂Pt[Ir₆(CO)₁₅] | ADS (THF) | 1.0 |
| | Pt (0.067) | | | | |
| 13. A | Ir (0.4) | 0.70 | [(C₂H₅)₄N]₂[Ir₆(CO)₁₅] | I.W. (CH₃OH) | 0.85 |
| 14. M | Ir (0.32) | 0.0 | Py₂Pt[Ir₂(CO)₇] | I.W. (THF) | 0.95 |
| | Pt. (0.16) | | | | |
| 15. E | Ir (0.32) | 0.70 | Py₂Pt[Ir₂(CO)₇] | I.W. (THF) | 0.95 |

TABLE IV-continued

CHARACTERIZATION OF Pt/Ir/Al₂O₃ CATALYSTS: APPARENT ACTIVE METAL SURFACE AREAS

| Catalyst | Metals (Wt. %)[a] | Chlorine (Wt %) | Precursors | Impregnation[b] Method | H/M[c] |
|---|---|---|---|---|---|
| | Pt (0.16) | | | | |

[a]In all cases analyzed, the actual metal loadings were in good agreement with the nominal values.
[b]I.W. = incipient wetness, ADS = adsorption from an overstanding solution.
[c]H/M = the ratio of hydrogen atoms absorbed to total number of metal atoms present on catalyst.

TABLE V

COMPARISON OF 0.4% Ir/0.067% Pt/0.47% Cl/Al₂O₃ CATALYSTS: n-HEPTANE DEHYDROCYCLIZATION
Conditions: 900° F. 200 psig, W/hr/W = 20.0
$H_2/C_7$ = 5.6, 2.74 gm Catalyst

| Catalyst | hr on feed | Conversion (%) | Selectivities (%)[c] Toluene | C₄ | i-C₇ | Coke[d] (%) |
|---|---|---|---|---|---|---|
| VII[a] | 22 | 92.7 | 14.2 | 60.9 | 4.01 | |
| | 39 | 86.8 | 14.2 | 51.3 | 7.96 | |
| | 47 | 88.3 | 21.3 | 46.6 | 8.35 | |
| | 48 | 88.8 | 22.8 | 43.5 | 8.42 | |
| | 63 | 75.0 | 25.4 | 24.9 | 19.1 | |
| | 64 | 77.2 | 25.1 | 25.6 | 18.9 | |
| | 69 | 76.8 | 24.2 | 24.6 | 19.4 | |
| | 70 | 76.4 | 24.7 | 24.8 | 19.8 | |
| | 87 | 73.8 | 25.7 | 23.0 | 20.6 | |
| | 88 | 73.6 | 24.9 | 22.9 | 20.9 | |
| | 92 | 73.0 | 24.8 | 22.1 | 21.0 | |
| | 94 | 73.2 | 24.1 | 23.1 | 22.0 | |
| | 112 | 72.1 | 22.5 | 23.0 | 23.7 | |
| | 113 | 72.2 | 24.6 | 21.9 | 22.7 | |
| | 114 | 72.7 | 24.3 | 21.5 | 22.6 | |
| | 137 | 71.6 | 23.8 | 22.1 | 23.4 | |
| | 144 | 68.1 | 24.4 | 20.7 | 24.9 | |
| | 159 | 67.2 | 22.3 | 21.6 | 26.6 | |
| | 165 | 65.0 | 23.1 | 19.9 | 27.3 | |
| | 167 | 65.6 | 22.2 | 20.7 | 27.4 | |
| | 183 | 66.2 | 20.4 | 22.1 | 27.7 | |
| | 189 | 65.8 | 21.4 | 21.0 | 27.3 | |
| | 207 | 67.1 | 21.8 | 21.3 | 26.8 | |
| | 209 | 67.4 | 21.7 | 20.6 | 26.2 | 1.20 |
| L[b] plus 0.47% Cl | 37 | 81.2 | 22.7 | 36.0 | 13.3 | |
| | 49 | 72.9 | 24.4 | 24.6 | 19.6 | |
| | 61 | 73.8 | 24.3 | 24.6 | 19.7 | |
| | 63 | 71.5 | 24.0 | 23.9 | 21.1 | |
| | 89 | 72.5 | 24.9 | 23.9 | 20.2 | |
| | 91 | 73.3 | 24.0 | 23.4 | 20.3 | |
| | 110 | 77.4 | 24.6 | 26.6 | 17.1 | |
| | 112 | 75.7 | 26.2 | 27.6 | 18.7 | |
| | 114 | 78.0 | 24.5 | 27.0 | 16.6 | |
| | 115 | 78.1 | 24.4 | 27.0 | 16.5 | |
| | 116 | 77.9 | 24.3 | 27.0 | 16.6 | |
| | 132 | 78.9 | 25.0 | 27.7 | 15.6 | |
| | 135 | 77.6 | 25.3 | 27.1 | 16.3 | |
| | 157 | 74.1 | 25.3 | 24.7 | 19.2 | |
| | 158 | 74.7 | 24.0 | 25.3 | 19.2 | |
| | 163 | 74.8 | 26.1 | 24.7 | 19.3 | |
| | 180 | 72.7 | 25.7 | 24.3 | 19.8 | |
| | 185 | 72.1 | 25.5 | 24.0 | 20.2 | |
| | 186 | 72.7 | 25.7 | 24.3 | 19.8 | |
| | 187 | 73.3 | 25.0 | 24.0 | 19.6 | |
| | 205 | 73.4 | 24.7 | 25.1 | 20.1 | |
| | 206 | 73.2 | 25.1 | 24.6 | 20.1 | 0.71 |

[a]Standard catalyst: Prepared by aqueous impregnation of η-Al₂O₃ with chloroiridic and chloroplatinic acids.
[b]Cluster catalyst: Prepared by impregnation of η-Al₂O₃ with a tetrahydrofuran solution of (pyridine)₂Pt[Ir₆(CO)₁₅].
[c]Selectivities are based upon the fraction of n-heptane converted.
[d]Spent catalysts were analyzed for coke after 210 hours on feed.

TABLE VI

COMPARISON OF 0.32% Ir/0.16% Pt/η-Al₂O₃ CATALYST: n-HEPTANE DEHYDROCYCLIZATION
Conditions: 900° F. 200 psig, W/hr/W = 20.0
$H_2/C_7$ = 5.0 1.0 gm Catalyst

| Catalyst | hr on feed | Conversion (%) | Selectivities (%)[d] Toluene | C₄⁻ | i-C₇ | Coke[e] (%) |
|---|---|---|---|---|---|---|
| VIII[a] | 22.75 | 71.8 | 19.8 | 30.6 | 31.2 | |
| | 24.25 | 70.1 | 19.2 | 28.4 | 33.4 | |
| | 44.00 | 65.6 | 17.9 | 28.8 | 36.9 | |
| | 49.75 | 63.9 | 18.1 | 27.7 | 36.8 | |
| | 65.25 | 63.9 | 17.1 | 25.2 | 41.7 | |
| | 69.50 | 63.1 | 16.8 | 24.9 | 41.7 | |
| | 93.75 | 60.3 | 16.6 | 24.8 | 42.1 | 1.2 |
| M[b] | 20.75 | 67.8 | 19.0 | 32.7 | 26.7 | |
| | 22.75 | 67.6 | 17.7 | 35.9 | 26.5 | |
| | 44.25 | 61.3 | 18.5 | 31.0 | 31.5 | |
| | 49.00 | 60.5 | 18.0 | 30.8 | 32.3 | |
| | 68.00 | 58.6 | 17.3 | 31.1 | 32.9 | |
| | 75.00 | 57.8 | 17.9 | 30.1 | 33.5 | |
| | 93.00 | 56.1 | 17.2 | 30.2 | 34.3 | 1.5 |
| M[c] plus 0.5% Cl | 18.00 | 73.3 | 19.8 | 31.4 | 28.0 | |
| | 20.75 | 70.5 | 19.5 | 30.4 | 29.6 | |
| | 40.00 | 66.1 | 17.5 | 31.5 | 34.1 | |
| | 49.75 | 65.9 | 17.4 | 31.4 | 34.1 | |
| | 64.75 | 61.0 | 17.1 | 31.5 | 38.5 | |
| | 69.25 | 62.8 | 17.6 | 29.0 | 35.3 | |
| | 97.50 | 61.4 | 17.6 | 31.9 | 35.2 | 2.1 |

[a]Standard catalyst: Prepared by aqueous impregnation of η-Al₂O₃ with chloroiridic and chloroplatinic acids.
[b]Cluster catalyst: Prepared by impregnation of η-Al₂O₃ with a tetrahydrofuran solution of (pyridine)₂Pt[Ir₂(CO)₇].
[c]Cluster catalyst + 0.5% chloride: Prepared by treating M with aqueous HCl.
[d]Selectivities based upon fraction of n-heptane converted.
[e]The spent catalysts were analyzed for coke after 100 hours on feed.

TABLE VII n-HEPTANE DEHYDROCYCLIZATION EMPLOYING A 0.33% Ru/0.22% Pt/Al₂O₃ CATALYST
Conditions: 900° F., 200 psig, W/hr/W = 20
$H_2/C_7$ = 5.0, 1.0 gm Catalyst

| Catalyst | hr on feed | Conversion (%) | Selectivities (%)[b] Toluene | C₄⁻ | i-C₇ |
|---|---|---|---|---|---|
| H[a] | 22.5 | 55.9 | 2.83 | 50.5 | 38.1 |
| | 42.5 | 41.28 | 2.76 | 29.1 | 59.9 |
| | 46.5[c] | 58.7 | 5.66 | 29.1 | 52.1 |

[a]Cluster catalyst: Prepared by impregnating η-Al₂O₃ with a tetrahydrofuran solution of (pyridine)₃Pt[Ru₃(CO)₁₂].
[b]Selectivities are based upon the fraction of n-heptane converted.
[c]Reaction temperature increased to 950° F.

TABLE VIII

COMPARISON OF 0.4% Ir/0.067% Pt/0.7 Cl/Al₂O₃ CATALYST: BAYWAY NAPHTHA REFORMING[a]
Conditions: 200 psig, w/hr/w = 2.26
6000 SCF H₂/BBL, 5.0 gm. catalyst

| Catalyst | Time (hr) | T °F. | RON | RCA | (%) Coke. | (%) Cl[d] |
|---|---|---|---|---|---|---|
| III[b] | 0–23 | 907 | 106.0 | 380 | | |
| | 23–47 | 910 | 104.7 | 259 | | |
| | 47–71 | 912 | 103.0 | 177 | | |
| | 71–92 | 909 | 102.5 | 167 | | |
| | 92–117 | — | — | — | | |

TABLE VIII-continued
COMPARISON OF 0.4% Ir/0.067% Pt/0.7 Cl/Al$_2$O$_3$ CATALYST: BAYWAY NAPHTHA REFORMING[a]
Conditions: 200 psig, w/hr/w = 2.26
6000 SCF H$_2$/BBL, 5.0 gm. catalyst

| Catalyst | Time (hr) | T °F. | RON | RCA | (%) Coke. | (%) Cl[d] |
|---|---|---|---|---|---|---|
| | 117–143 | 909 | 104.9 | 281 | | |
| | 143–167 | 910 | 104.3 | 238 | | |
| | 167–191 | 910 | 103.2 | 186 | | |
| | 191–215 | 910 | 103.0 | 180 | | |
| | 215–239 | 910 | 103.2 | 186 | | |
| | 239–264 | 912 | 103.5 | 188 | | |
| | 264–288 | 914 | 104.0 | 192 | 1.34 | 0.59 |
| D[c] | 0–18 | 905 | 104.7 | 298 | | |
| | 18–50 | 910 | 104.8 | 264 | | |
| | 50–70 | 905 | 104.2 | 269 | | |
| | 70–94 | 907 | 104.4 | 269 | | |
| | 94–118 | 907 | 105.0 | 307 | | |
| | 118–142 | 905 | 105.3 | 342 | | |
| | 142–166 | 905 | 105.3 | 342 | | |
| | 166–192 | 910 | 106.7 | 410 | | |
| | 192–216 | 910 | 106.7 | 410 | | |
| | 216–238 | 907 | 106.3 | 404 | | |
| | 238–262 | 909 | 106.7 | 247 | | |
| | 262–286 | 889 | 103.9 | 411 | 0.94 | 0.52 |

[a]The Bayway naphtha is characterized as follows: 47.2% paraffins, 42.2% naphthenes and 10.5% aromatics, d$_{75°F.}$ = 0.7539, RON = 54, 0.5 ppm sulfur (by thiophene addition).
[b]Standard catalyst was prepared by the impregnation of 1/16 inch γ-Al$_2$O$_3$ extrudate (179 m$^2$/gm) with chlorioridic and chloroplatinic acid solutions. the chlorine content was adjusted to 0.7 wt. % by the addition of aqueous HCl.
[c]Cluster catalyst was prepared by the impregnation of a dry 0.7 wt. % Cl/γ-Al$_2$O$_3$ support (178 m$^2$/gm) with a tetrahydrofuran solution of (pyridine)$_2$Pt[Ir$_6$(CO)$_{15}$]. The final catalyst was in the form of 10/20 mesh particles.
[d]The spent catalysts were analyzed for coke and chlorine content.

TABLE IX
COMPARISON OF 0.4% Ir/0.067% Pt/0.7% Cl/Al$_2$O$_3$ CATALYSTS: BAYWAY NAPHTHA REFORMING[a]
Conditions: 200 psig, w/hr/w = 2.26
6000 SCF H$_2$/BBL, 5.0 gm catalyst

| Catalyst | Time (hr) | T°]F. | RON | RCA |
|---|---|---|---|---|
| II[b] | 0–20 | 909 | 104.0 | 229 |
| | 20–44 | — | — | — |
| | 44–67 | 907 | 102.6 | 177 |
| | 67–90 | 909 | 102.5 | 165 |
| | 90–117 | 907 | 102.4 | 170 |
| | 117–139 | 910 | 102.0 | 143 |
| | 139–165 | 910 | 102.3 | 152 |
| | 165–189 | 912 | 103.3 | 179 |
| B[c] | 0–19 | 905 | 106.3 | 428 |
| | 19–39 | 907 | 104.9 | 293 |
| | 39–71 | 907 | 103.9 | 255 |
| | 71–91 | 905 | 104.2 | 269 |
| | 91–115 | 909 | 106.0 | 354 |
| | 115–140 | 918 | 107.4 | 411 |
| | 140–164 | 909 | 106.7 | 427 |
| | 164–188 | 901 | 105.7 | 421 |

[a]Bayway feed: 47.2% paraffins, 42.2% naphthenes, 10.5% aromatics, d$^{75° F.}$ = 0.7539, RON = 0.5 ppm total sulfur
[b]Standard catalyst was prepared by impregnation of 1/16 inch γ-Al$_2$O$_3$ extrudate (179 m$^2$/gm) with chlorioridic and chloroplatinic acid solutions. The chlorine content was adjusted to 0.7 wt. % by the addition of aqueous HCl.
[c]Cluster catalyst was prepared by the impregnation of a dry 0.7 wt. % Cl/γ-Al$_2$O$_3$ extrudate (179 m$^2$/gm) with a tetrahydrofuran solution of (pyridine)$_2$Pt[Ir$_6$(CO)$_{15}$].

TABLE X
COMPARISON OF 0.4% Ir/0.7% Cl/Al$_2$O$_3$ CATALYSTS: BAYWAY NAPHTHA REFORMING[a]
Conditions: 200 psig, W/hr/W = 2.26
6000 SCF H$_2$/BBL, 5.0 gm Catalyst

| Catalyst | Time (hr) | T °F. | RON | RCA | (%) Coke | (%) Cl[d] |
|---|---|---|---|---|---|---|
| I[b] | 0–23 | 910 | 106+ | — | | |
| | 17–46 | 910 | 106.3 | 360 | | |
| | 46–70 | 910 | 103.5 | 198 | | |
| | 70–93 | 910 | 103.1 | 182 | | |
| | 93–116 | 909 | 103.4 | 202 | | |
| | 116–140 | 910 | 103.7 | 205 | | |
| | 140–166 | 909 | 104.2 | 224 | | |
| | 166–190 | 909 | 104.5 | 258 | | |
| | 190–214 | 912 | 105.1 | 263 | 1.28 | 0.66 |
| A[c] | 0–23 | 905 | 106.7 | 370 | | |
| | 23–43 | 905 | 104.3 | 215 | | |
| | 43–68 | 905 | 104.1 | 202 | | |
| | 68–92 | 912 | 104.3 | 177 | | |
| | 92–116 | 912 | 105.2 | 216 | | |
| | 116–140 | 910 | 103.8 | 166 | | |
| | 140–164 | 912 | 103.0 | 132 | | |
| | 164–188 | 910 | 103.0 | 139 | | |
| | 188–213 | 914 | 99.7 | 62 | | |
| | 213–236 | 909 | 98.4 | 58 | | |
| | 236–259 | 910 | 99.3 | 64 | 1.54 | 0.65 |

[a]Bayway feed: 47.2% paraffins, 42.2% naphthenes, 10.5% aromatics, d$_{75°F.}$ = 0.7539, RON = 54, 0.5 ppm total sulfur.
[b]Standard catalyst was prepared by impregnating 1/16 inch γ-Al$_2$O$_3$ extrudate (178 m$^2$/gm) with chloroidic acid solution. The chlorine content was adjusted to 0.7 wt. % by the addition of aqueous HCl.
[c]Cluster catalyst was prepared by impregnating a dry 0.7 wt. % Cl/γ-Al$_2$O$_3$ support (167 m$^2$/gm) with a methanol solution of [(C$_2$H$_5$)$_4$N]$_2$[Ir$_6$(CO)$_{15}$].
[d]Spent catalysts were analyzed for wt. % carbon and chlorine.

TABLE XI
COMPARISON OF 0.32 Ir/0.16% Pt/0.7% Cl/Al$_2$O$_3$ CATALYSTS: BAYWAY NAPHTHA REFORMING[a]
Conditions: 200 psig, W/hr/W = 2.26
6000 SCF H$_2$/BBL, 5.0 gm Catalyst

| Catalyst | Time (hr) | T °F. | RON | RCA | %[e] Coke | %[d] Cl |
|---|---|---|---|---|---|---|
| IV[b] | 0–20 | 910 | 106.0 | 340 | | |
| | 20–45 | 909 | 104.9 | 281 | | |
| | 45–69 | 909 | 104.7 | 269 | | |
| | 69–89 | 910 | 103.8 | 212 | | |
| | 89–114 | 912 | 103.9 | 205 | | |
| | 114–141 | 910 | 103.5 | 198 | | |
| | 141–164 | 909 | 103.3 | 197 | | |
| | 164–185 | 907 | 102.2 | 161 | | |
| | 185–213 | 907 | 101.9 | 152 | | |
| | 213–237 | 907 | 101.6 | 148 | | |
| | 237–257 | 910 | 101.8 | 137 | | |
| | 257–282 | 909 | 101.7 | 139 | | |
| | 282–309 | 909 | 102.0 | 149 | | |
| | 309–332 | 910 | 102.1 | 147 | 1.50 | 0.42 |
| E[c] | 0–21 | 909 | 104.8 | 269 | | |
| | 21–45 | 909 | 105.2 | 302 | | |
| | 45–69 | 907 | 103.5 | 215 | | |
| | 69–93 | 909 | 103.3 | 197 | | |
| | 93–113 | 910 | 103.9 | 216 | | |
| | 113–138 | 914 | 103.5 | 179 | | |
| | 138–166 | 910 | 103.9 | 216 | | |
| | 166–189 | 909 | 103.9 | 225 | | |
| | 189–214 | 907 | 103.0 | 193 | | |
| | 214–237 | 909 | 104.0 | 229 | | |
| | 237–261 | 306–104.3 | 238 | | | |
| | 261–285 | 910 | 104.3 | 238 | | |
| | 285–306 | 910 | 104.4 | 243 | | |
| | 305–333 | 910 | 104.4 | 243 | 1.94 | 0.48 |

[a]Bayway feed: 47.2% paraffins, 42.2% naphthenes, 10.5% aromatcis d$^{75° F.}$ = 0.7539, RON = 54, 0.5 ppm total sulfur.
[b]Standard catalysts was prepared by impregnating γ-Al$_2$O$_3$ powder (154 m$^2$/gm) with chlorioridic and chloroplatinic acid solutions. The chlorine content was adjusted to 0.7 wt. % by the addition of aqueous HCl.
[c]Cluster catalyst was prepared by impregnating a dry 0.7%/Cl$_γ$-Al$_2$O$_3$ powder (167 m$^2$/gm) with a tetrahydrofuran solution of (pyridine)$_2$Pt[Ir$_2$(CO)$_7$].
[d]Spent catalysts were analyzed for wt. % carbon and chlorine.

What is claimed is:
1. A heteronuclear noble metal carbonyl cluster complex of the formula:

$((C_6H_5)_3P)_2Pt[Ir(CO)_3P(C_6H_5)_3]_2$ which exhibits the following characteristic infrared pattern (cm$^{-1}$) in THF solution:
2014 sh
1995 sh
1982 sh
1962 vs
1934 sh
1906 m-s
1800 w
1764 sh.

2. A heteronuclear noble metal carbonyl cluster complex of the formula:

$((C_6H_5)_3P)_2Rh(CO)[Ir(CO)_4]$ which exhibits the following characteristic infrared pattern (cm$^{-1}$) in THF solution:
2042 w
1995 sh
1987 vs
1962 sh
1932 m.

* * * * *